(12) United States Patent
Buchlovic et al.

(10) Patent No.: US 11,390,593 B2
(45) Date of Patent: Jul. 19, 2022

(54) PROCESS FOR PREPARING OZANIMOD

(71) Applicant: Synthon B.V., Nijmegen (NL)

(72) Inventors: Marian Buchlovic, Blansko (CZ); Lenka Chalupova, Blansko (CZ); Libor Vyklicky, Blansko (CZ); Jiri Bartl, Blansko (CZ)

(73) Assignee: Synthon B.V., Nijmegen (NL)

( * ) Notice: Subject to any disclaimer, the term of this patent is extended or adjusted under 35 U.S.C. 154(b) by 0 days.

(21) Appl. No.: 17/311,094

(22) PCT Filed: Dec. 5, 2019

(86) PCT No.: PCT/EP2019/083801
§ 371 (c)(1),
(2) Date: Jun. 4, 2021

(87) PCT Pub. No.: WO2020/115200
PCT Pub. Date: Jun. 11, 2020

(65) Prior Publication Data
US 2021/0363117 A1    Nov. 25, 2021

(30) Foreign Application Priority Data

Dec. 7, 2018  (EP) ..................................... 18211127

(51) Int. Cl.
*C07D 271/06* (2006.01)
*C07D 263/22* (2006.01)

(52) U.S. Cl.
CPC ......... *C07D 271/06* (2013.01); *C07D 263/22* (2013.01)

(58) Field of Classification Search
CPC ............................ C07D 271/06; C07D 263/22
See application file for complete search history.

(56) References Cited

FOREIGN PATENT DOCUMENTS

| CN | 108727292 A | 11/2018 |
| EP | 3406142 A1 | 11/2018 |
| WO | WO 2011/060392 A1 | 5/2011 |
| WO | WO 2018/215807 A1 | 11/2018 |

*Primary Examiner* — Shawquia Jackson
(74) *Attorney, Agent, or Firm* — Buscher Patent PLLC

(57) ABSTRACT

The presented invention relates to a process for preparation of compound of formula (1) or a salt thereof (i.e.) ozanimod: (1). The invention also relates to intermediates used in the process.

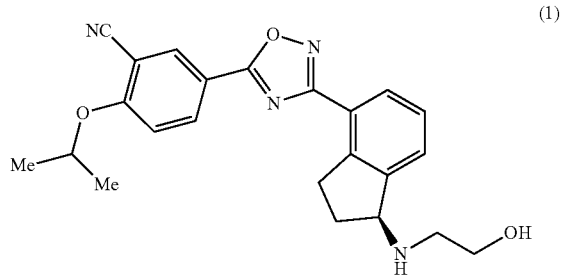

(1)

26 Claims, 16 Drawing Sheets

PROCESS FOR PREPARING OZANIMOD

BACKGROUND OF THE PRESENT INVENTION

This invention relates to an improved process of preparation of ozanimod, compound of formula (1) or a salt thereof:

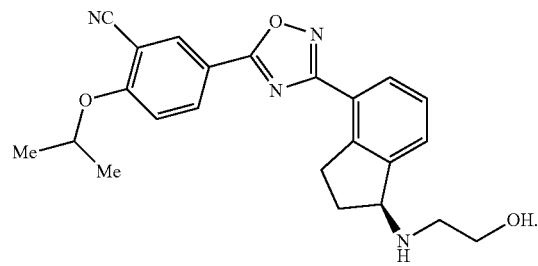
(1)

Ozanimod, 5-[3-[1(S)-(2-Hydroxyethylamino)-2,3-dihydro-1H-inden-4-yl]-1,2,4-oxadiazol-5-yl]-2-isopropoxy-benzonitrile, is an oral agonist of the lysophospholipid S1P1 and S1P5 receptors. Ozanimod is in pre-registration used for the treatment for patients with relapsing multiple sclerosis and in phase III for the treatment of ulcerative colitis and for the treatment of Crohn's disease.

Ozanimod was disclosed in WO2011060392 application. The application also describes a process for preparation of ozanimod. The intermediates used in the process are oily compounds that were purified by column chromatography. Chromatographic purification steps are tedious and expensive process steps on an industrial scale.

Therefore, there is a need for alternative process that does not comprise chromatographic purification and provides ozanimod in sufficient purity and yield.

BRIEF DESCRIPTION OF THE INVENTION

The presented invention relates to a process for preparation of compound of formula (1) or a salt thereof,

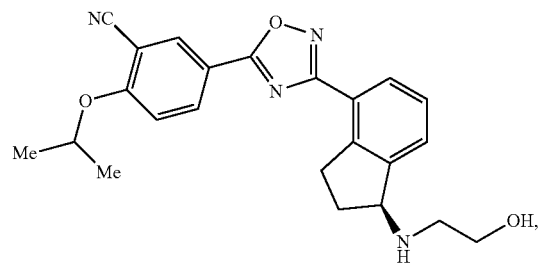
(1)

comprising:

I. Reacting a compound (2) or a salt thereof with compound (3),

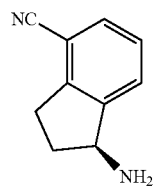
(2)

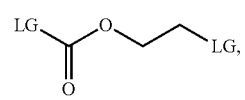
(3)

LG is a leaving group independently selected from Cl or Br or I or an ester selected from methoxy or ethoxy or tosylate or mesylate or benzenesulfonate or triflate in a solvent in a presence of a base;

II. Adding a base selected from an alcoholate or a hydride or an organometal or a hydroxide or a salt of an organic amide or 1,8-Diazabicyclo[5.4.0]undec-7-ene or 1,5-Diazabicyclo(4.3.0)non-5-ene or 1,4-diazabicyclo[2.2.2]octane into the reaction mixture of step I to provide compound (4),

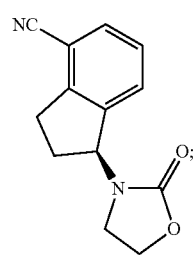
(4)

III. Reacting compound (4) with hydroxylamine or a salt thereof in a solvent to provide compound (5),

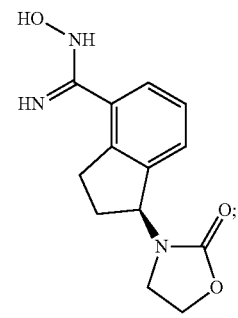
(5)

IV. Reacting compound (5) with compound (6) in a presence of coupling agent in a solvent to provide compound (7),

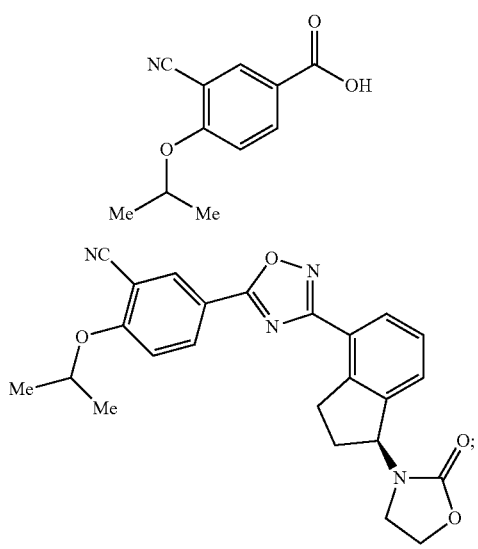

V. Reacting compound (7) in a presence of a compound of formula $(R)_3SiOM$, R is selected from $R_1$-$R_5$ alkyl or aryl and M is selected from Na or K or Li in a solvent to provide compound (1).

The presented invention also relates to intermediate compounds (4) and (5).

The presented process does not comprise chromatographic purification and provides ozanimod or a salt thereof in good purity and yield.

DETAILED DESCRIPTION OF THE INVENTION

Figure 1:
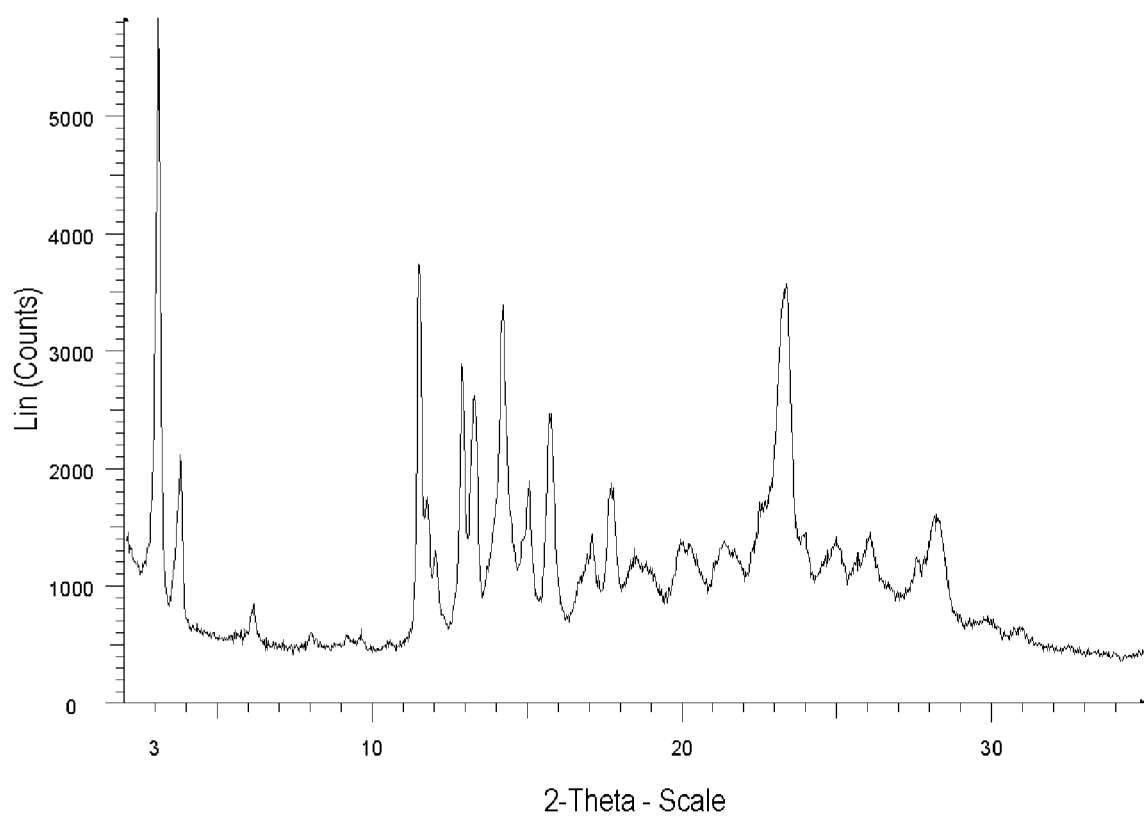
FIG. 1 depicts the X-Ray Powder Diffractogram (XRPD) of ozanimod salt with $H_2SO_4$ obtainable according to the Example 7.

The presented invention relates to a process for preparation of compound of formula (1) or a salt thereof,

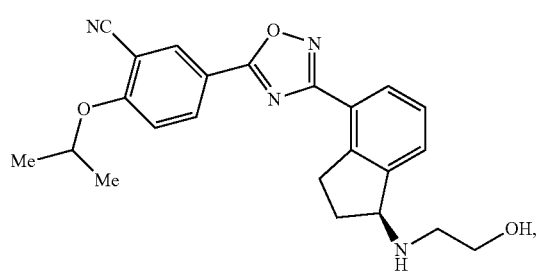

comprising:
I. Reacting a compound (2) or a salt thereof with compound (3):

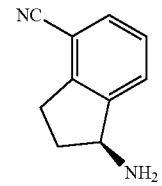

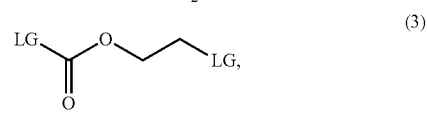

LG is a leaving group independently selected from Cl or Br or I or an ester selected from methoxy or ethoxy or tosylate or mesylate or benzenesulfonate or triflate in a solvent in a presence of a base;

II. Adding a base selected from an alcoholate or a hydride or an organometal or a hydroxide or a salt of an organic amide or 1,8-Diazabicyclo[5.4.0]undec-7-ene or 1,5-Diazabicyclo(4.3.0)non-5-ene or 1,4-diazabicyclo[2.2.2]octane into the reaction mixture of step I to provide compound (4),

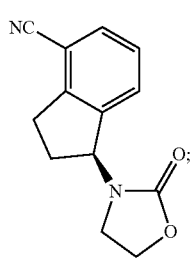

(4)

III. Reacting compound (4) with hydroxylamine or a salt thereof in a solvent to provide compound (5);

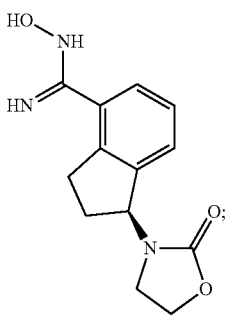

(5)

IV. Reacting compound (5) with compound (6) in a presence of coupling agent in a solvent to provide compound (7), (6)

(7)

V. Reacting compound (7) in a presence of a compound of formula $(R)_3SiOM$, R is selected from $R_1$-$R_5$ alkyl or aryl and M is selected from Na or K or Li in a solvent to provide compound (1).

The starting compounds (2) and (3) are commercially available. Compound (2) can also be prepared by deprotection of compound (8) in a solvent:

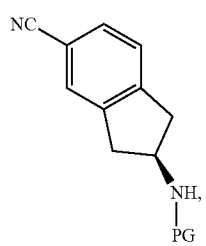

(8)

wherein PG is a suitable amino protecting group, for example selected from carbamates, amides, N-alkyl andN-aryl amines, quaternary ammonium salts, N-sulfonyl derivatives, halogen, such as phthaloyl (Phth), tetrachlorophthaloyl (TCP), dithiasuccinyl (Dts), Trifluoroacetyl, methoxycarbonyl, ethoxycarbonyl, tert-Butoxycarbonyl (Boc), Benzyloxycarbonyl (Cbz), allyloxycarbonyl (Allot), 9-fluorenylmethoxycarbonyl (Fmoc), 2-(trimethylsilylethoxycarbonyl (Teoc), 2,2,2-trichloroethoxycarbonyl (Troc), phenylsulfonyl, p-tolylsulfonyl (Ts), 2- and 4-nitrophenylsulfonyl (Ns), 2-(trimethylsilylethylsulfonyl (SES), benzyl (Bn), diphenylmethyl (Dpm), p-methoxybenzyl (PMB), 3,4-dimethoxy benzyl (DMPM), p-methoxyphenyl (PMP) and allyl. PG is preferably selected from Boc and Cbz.

The suitable solvent can be for example an alcohol (for example methanol, ethanol, propanol, butanol) or a haloalkane (for example dichloromethane, chloroform) or an acetate (for example ethylacetate, isopropyl acetate, butyl acetate, isobutyl acetate, propyl acetate) or an ether (for example diethyl ether, methyl tert-butyl ether) or tetrahydrofurane or 2-methyl tetrahydrofurane or dimethylformamide or dimethysulfoxide and a combination thereof.

The compound (8) can be deprotected by using any suitable for example acidic conditions (using for example trifluoroacetic acid, methanesulfonic acid, HCl, $H_2SO_4$, HBr, pentafluoropropionic acid, benzenesulfonic acid) or by catalytic hydrogenation or by deprotection in a base (for example in sodium or potassium hydroxide).

The compound (2) can be used in reaction step I as a free compound or as a salt, for example in form of HCl or HBr salt. Reaction step I is done in a suitable solvent, for example selected from tetrahydrofurane or 2-methyl tetrahydrofurane or toluene or acetonitrile or dimethylformamide or a mixture of the solvent with water, in a presence of a base.

Advantageously the reaction step I is performed in two phases system of the solvent that is immiscible with water (such as 2-methyl tetrahydrofurane or toluene) and water. Preferably a mixture of water and 2-methyl tetrahydrofurane is used. The volume ratio between the solvent and water can be between 1.5:1 and 5:1, preferably it is between 2:1 and 3:1. To improve the reaction yield and conversion a phase transfer catalyst can be used. Use of two-phases system improves the purity of obtained product and simplifies the isolation of the product.

The suitable base can be selected from:
i. An organic base, such as an amine (for example diethylamine, triethylamine, iso-propyl diethyl amine) or 1,8-Diazabicyclo[5.4.0]undec-7-ene or 1,5-Diazabicyclo(4.3.0)non-5-ene or 1,4-diazabicyclo[2.2.2]octane or a phosphazene base (such as tert-Butyliminotris(dimethylamino)phosphorane, tert-Butylimino-tri (pyrrolidino)phosphorane, 2-tert-Butylimino-2-diethylamino-1,3-dimethyl-perhydro-1,3,2-diazaphosphorine, 1-tert-Butyl-4,4,4-tris (dimethylamino)-2,2-bis[tris(dimethylamino)-phosphoranylidenamino]-2λ5,4λ5-catenadi (phosphazene)) or an organometal (such as MeLi, BuLi, t-BuLi, MeMgBr, EtMgCl, i-PrMgBr, PhMgBr, hexyllithium, octyllithium) or an amide (such as Lithium diisopropylamide, Lithium bis(trimethylsilyl) amide, sodium bis(trimethylsilyl)amide, potassium bis (trimethylsilyl)amide) or an alcoholate (such as sodium or potassium methanolate or sodium or potassium ethanolate) or a hydride (such as sodium or potassium hydride); or ii. An inorganic base for example a hydroxide (such as sodium hydroxide or potassium hydroxide) or a carbonate (such as sodium carbonate, potassium carbonate) or a hydrogencarbonate (such as sodium hydrogencarbonate or potassium hydrogencarbonate).

The base is preferably triethylamine or potassium carbonate.

The concentration of compound (2) in the solvent can be between 0.05 and 0.5 g/ml, preferably it is between 0.1 and 0.2 g/ml. The molar ratio between compounds (2) and (3) can be between 1:1 and 1:3, preferably it is between 1:1 and 1:1.5. The molar ratio between compound (2) and the base can be between 1:1.5 and 1:5, preferably between 1:2 and 1:3. The compound (2) is mixed with the solvent and the base is added. The base can be also mixed with water and added to the mixture of compound (2) in the solvent. To improve the reaction yield and conversion a phase transfer catalyst can be used. The phase transfer catalyst improves the passing of a reagent such as the base or reaction products from one phase (water) into the other (organic phase). The examples of phase transfer catalyst that can be used in the presented invention are: tetra alkyl ammonium salts (such as tetra butyl ammonium chloride or tetra butyl ammonium iodide or tetra methyl ammonium iodide or di decyl di methyl ammonium bromide) or aryl tri alkyl ammonium salts (such as benzyl tri methyl ammonium chloride or benzyl tri methyl ammonium hydroxide).

Use of two-phases system (water and water immiscible solvent) improves the purity of obtained product and simplifies the isolation of the product.

The temperature of the mixture is set to between −10° C. and 40° C., preferably to a temperature between 0 and 15° C. and compound (3) is slowly, preferably in the course of 10 or 20 or 30 or 40 or 50 or 60 minutes, more preferably drop-wise added to the reaction mixture. Reaction mixture is then stirred at a temperature between −10° C. and 30° C., preferably at a temperature between 20 and 20° C. for between 30 minutes and 10 hours, preferably for 0.5 to 5 hours, more preferably for 0.5 to 2 hours. The reaction progress can be monitored by a suitable analytical technique e.g. by HPLC or GC. After the reaction is finished, the mixture can be optionally filtered and the filtrated mass is washed by a suitable solvent, for example with tetrahydrofurane (THF). The temperature of obtained mother liquor is set to a temperature between −10° C. and the reflux temperature of the used solvent and used in the subsequent step II. Alternatively, when two-phases system of the solvent and water is used, the mixture is stirred to obtain a solution preferably at a temperature between 40° C. and the reflux temperature of used solvent, preferably between 50° C. and 80° C., and the phases were separated at the elevated temperature. Obtained organic phase was used in subsequent step II.

To the filtrate or obtained organic phase at the elevated temperature a strong base selected from an alcoholate (such as sodium or potassium methanolate or sodium or potassium ethanolate) or a hydride (such as sodium or potassium hydride) or an organometal (such as butyl lithium) or a hydroxide (such as sodium or potassium hydroxide) or a salt of an organic amide (such as sodium bis(trimethylsilyl) amide or lithium bis(trimethylsilyl)amide or sodium amide or lithium diisopropyl amide or lithium diethylamide) or 1,8-Diazabicyclo[5.4.0]undec-7-ene or 1,5-Diazabicyclo (4.3.0)non-5-ene or 1,4-diazabicyclo[2.2.2]octane is added (step II), preferably it is a hydroxide, more preferably it is potassium hydroxide. The strong base can be added as a solution in used solvent or as a solution in water (to form a mixture of solvent and water, preferably two-phases system) or as a solid.

Alternatively, the base used in step I can correspond to the base used in step II.

The molar ratio between the compound (2) and the base can be between 1:1.2 and 1:4, preferably it is between 1:1.8 and 1:3, more preferably it is 1:2. The reaction is performed at a temperature between −10° C. and reflux temperature of used solvent, preferably at a temperature between 0° C. and reflux temperature of used solvent for 30 minutes to 10 hours, preferably for 1 to 5 hours, more preferably for 1 to 2 hours. The reaction progress can be monitored by a suitable analytical technique e.g. by HPLC or GC. After the reaction is finished, the temperature of the mixture is set to 20-25° C. and concentrated under vacuum to dryness. The rest is dissolved in a mixture of water and the water immiscible organic solvent such as ethylacetate or methylacetate or toluene or ether, preferably in water and ethylacetate. The organic phase is separated and the water phase is extracted with the organic solvent. Combined organic mixtures were dried, for example over $MgSO_4$, and evaporated to dryness to provide compound (4). Alternatively, when a mixture of a solvent and water is used, after the reaction is finished, the phases are separated at a temperature between 40° C. and 80° C., preferably between 60° C. and 70° C. Organic phase can be washed with water. The organic phase can be optionally concentrated to obtain compound (4) in a solid form or the solution can be used in subsequent reaction step III.

We have surprisingly found that compound (4) can be isolated in solid form in good yield and purity. The purity of compound (1) prepared from this solid form of compound (4) is high without a need to use column chromatography purification of either an intermediate or the final compound (1) as described in the prior art.

Compound (4) reacts in step III with hydroxylamine or a salt thereof in a suitable solvent to provide compound (5). Hydroxylamine can be present in a free form of in the form of a salt such as HCl salt. The hydroxylamine can also be used in the form of a water solution, for example in form of 50% solution. The suitable solvent can be selected from acetonitrile or an alcohol (for example methanol or ethanol or propanol or isopropanol or butanol or tert-butanol) or tetrahydrofurane or 2-methyl tetrahydrofurane or combination thereof. Advantageously a mixture of an alcohol (for example methanol or ethanol or propanol or isopropanol or butanol or tert-butanol) and tetrahydrofurane or 2-methyl tetrahydrofurane can be used. Preferably a mixture of ethanol and tetrahydrofurane or a mixture of isopropanol and 2-methyl tetrahydrofurane is used. The ratio (vol:vol) between the alcohol and tetrahydrofurane or 2-methyl tetrahydrofurane can be between 5:1 and 15:1, preferably it is between 7:1 and 11:1, more preferably it is 9:1.

The concentration of compound (4) in the solvent can be between 0.03 and 0.2 g/ml, preferably between 0.05 and 0.15 g/ml, more preferably between 0.07 and 0.11 g/ml.

The molar ratio between compound (4) and hydroxylamine can be between 1:1.1 and 1:3, preferably it is between 1:1.1 and 1:2. Most preferred ratio is 1:1.5. The mixture is heated at elevated temperature, for example at a temperature between 50° C. and the reflux temperature of used solvent mixture for between 3 and 48 hours, preferably for 4 to 24 hours. The reaction progress can be monitored by a suitable analytical technique, e.g. by HPLC or GC. After the reaction is finished, the mixture is cooled to a temperature between −10° C. and 30° C., preferably to 0 to 10° C. The mixture is filtered and the filtration cake is washed with a suitable solvent, for example with ethanol or isopropanol. The obtained solid compound (5) can be optionally dried.

Advantageously, the reaction steps I, II and III can be performed as one pot synthesis without isolation of reaction intermediates, preferably when two-phase reaction system is used in steps I and/or II. That simplifies the preparation process.

We have surprisingly found that compound (5) can be isolated in solid form in good yield and purity. The purity of compound (1) prepared from this solid form of compound (5) is high without a need to use column chromatography purification of either an intermediate or the final compound (1) as described in the prior art.

Compound (5) reacts in step IV with compound (6) in a presence of a coupling agent in a solvent to provide compound (7):

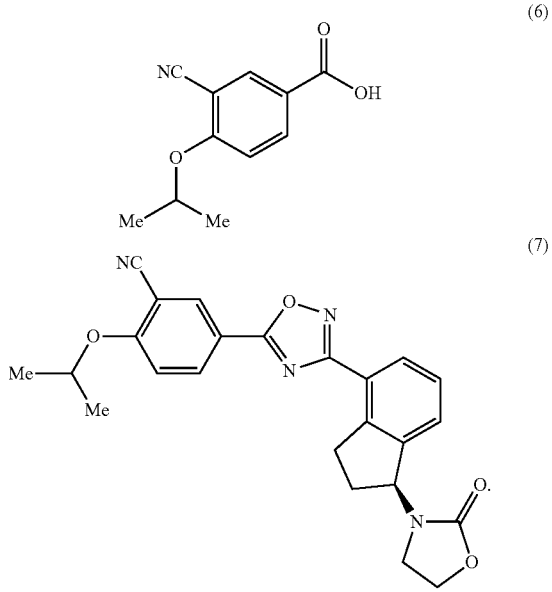

The solvent can be selected from for example N-methylpyrrolidone or an alcohol (for example methanol or ethanol or propanol or butanol) or an haloalkane (for example dichloromethane or chloroform) or an acetate (for example ethylacetate or isopropyl acetate or butyl acetate or isobutyl acetate or propyl acetate) or an ether (for example diethyl ether or methyl tert-butyl ether) or tetrahydrofurane or 2-methyl tetrahydrofurane or dimethyl-formamide or dimethysulfoxide or acetonitrile or 1,3-Dimethyl-3,4,5,6-tetrahydro-2(1H)-pyrimidinone (DMPU) and a combination thereof. The organic solvent can be also combined with water. The coupling agent can be for example DCC (dicyclohexylcarbodiimide), DIC (diisopropylcarbodiimide), HOBt (1-hydroxy-benzotriazole), HOAt (1-hydroxy-7-azabenzotriazole), BOP (benzotriazol-1-yloxy)tris(dimethylamio)phosphonium hexafluoro-phosphate), PyBOP (benzotriazol-1-yloxy)tris(pyrrolidino)phosphonium hexafluorophosphat, PyBroP (bromo)tris(pyrrolidino)phosphonium hexafluorophosphate), BroP (bromo)tris(dimethylamio) phosphonium hexafluorophosphate), HBTU (2-(1H-benzotriazole-1-yl)-1, 1,3,3-tetramethyluroniumhexafluorophosphate), CDI (1,1'-Carbonyldiimidazole), EDAC (N-(3-Dimethylaminopropyl)-N'-ethylcarbodiimide hydrochloride or a cyclic alkyltriphosphonate anhydride of general formula:

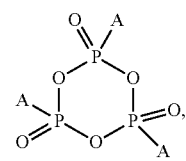

wherein A is C1-C3 alkyl group, preferably propyl and a combination thereof. The coupling agent is preferably CDI (1,1'-Carbonyldiimidazole).

Concentration of compound (5) in the solvent can be between 0.04 g/ml and 0.35 g/ml, preferably between 0.07 and 0.15 g/ml.

Concentration of compound (6) in the solvent can be between 0.04 g/ml and 0.25 g/ml, preferably between 0.06 and 0.11 g/ml.

Molar ratio between compound (5) and compound (6) can be between 1:0.7 and 1:2, preferably it is between 1:0.8 and 1:1.5. Most preferred ratio is 1:1.

The molar ratio between compound (5) and the coupling agent can be between 1:0.5 and 1:2, preferably it is between 1:0.8 and 1:1.5.

Compound (6) is mixed with the coupling agent in the solvent and the mixture is stirred at a temperature between 20° C. and 40° C., preferably at a temperature between 20 and 25° C. for between 1 and 5 hours, preferably for between 1 and 3 hours. Afterwards, compound (5) is added and the mixture. The mixture is stirred at a temperature between 20° C. and the reflux temperature of the used solvents for 5 to 24 hours. In one preferred embodiment of the invention the mixture after addition of the compound (5) is stirred for between 0.5 and 3 hours at a temperature between 20° C. and 25° C. and then at a temperature between 60° C. and the reflux temperature of used solvents, preferably at 80° C. for between 4.5 and 21 hours. The reaction progress can be monitored by a suitable analytical technique, e.g. by HPLC or GC. After the reaction is finished, water is added to the mixture to obtain suspension of compound (7). The volume ratio between the solvent used in the reaction step IV and added water can be between 2:1 and 5:1, preferably it is between 2.5:1 and 3.5:1. The suspension after addition of water is cooled at a temperature between −10° C. and 20° C., preferably at a temperature between 0 and 5° C. and stirred at this temperature for 1 to 5 hours. The suspension is filtered to provide compound (7) in a solid state. We have surprisingly found that compound (7) can be obtained in a solid form in good yield and purity. The purity of compound (1) prepared from this solid form of compound (7) is high without a need to use column chromatography purification of either an intermediate or the final compound (1) as described in the prior art.

Compound (7) is subsequently transformed into compound (1) in a presence of a compound of formula (R)₃SiOM, R is selected from R₁-R₅ alkyl or aryl and M is selected from Na or K or Li in a solvent to provide compound (1) in a solvent (step V). The compound of formula (R)₃SiOM can be alternatively prepared in situ by reaction between compound of formula (R)₃SiOH, R is selected from R₁-R₅ alkyl or aryl and a base comprising M cation, for example potassium or sodium or lithium alkoxide such as potassium tert-butoxide or sodium tert-butoxide or lithium tert-butoxide or sodium methoxide or potassium methoxide or lithium methoxide or sodium ethoxide or potassium ethoxide or lithium ethoxide.

As a solvent for example tetrahydrofurane or 2-methyl tetrahydrofurane or dioxane or dimethylformamide or dimethylacetamide or dimethylsulfoxide or a mixture thereof, preferably tetrahydrofurane can be used. The compound of formula (R)₃SiOM, R is selected from R₁-R₅ alkyl or aryl and M is selected from Na or K or Li, is preferably selected from (R)₃SiONa or (R)₃SiOK. More preferably it is sodium or potassium trimethylsilinoate of formula:

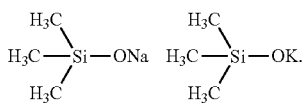

Advantageously compound of formula (R)3SiOH, R is selected from R₁-R₅ alkyl or aryl is added into the mixture. Preferably it is trialkylsilanol, more preferably trimethylsilanol. The ratio (vol:vol) between the solvent and the compound of formula (R)₃SiOH can be between 2:1 and 6:1, preferably it is between 3:1 and 5:1.

The concentration of compound (7) in the solvent can be between 0.08 g/ml and 0.3 g/ml, preferably it is between 0.09 and 0.2 g/ml. The molar ratio between compound (7) and the compound of formula (R)₃SiOM can be between 1:2 and 1:6, preferably it is between 1:3 and 1:5. The reaction mixture is stirred at a temperature between 50° C. and the reflux temperature of the used solvent for between 0.5 and 10 hours, preferably for between 1 and 3 hours. The solvents are distilled of to obtain compound of formula (1).

Advantageously compound (1) prepared according to process of the invention can be transformed to a salt with sulfuric acid or citric acid or formic acid or benzoic acid or acetic acid or oxalic acid or H₃PO₄ or HCl. The salt can be prepared by contacting ozanimod (compound (1)) with the corresponding acid in a solvent comprising an alcohol (such as isopropanol or methanol or ethanol or propanol or butanol or tert-butanol) or 2-methyl tetrahydrofurane or tetrahydrofurane or methanol or water or a mixture thereof, heating the mixture at a temperature between 70° C. and the reflux temperature of used solvent and subsequent cooling of the mixture to a temperature between 0° C. and 25° C., preferably at a temperature between 20 and 25° C. and stirring at this temperature for between 1 and 10 hours, preferably between 1 and 3 hours, to obtain a crystalline form of ozanimod salt with the corresponding acid. The concentration of ozanimod in the solvent can be between 0.01 and 0.1 g/ml, preferably it is between 0.03 and 0.05 g/ml. The molar ratio between ozanimod and the acid can be between 1:1 and 1:5, preferably it is between 1:1.05 and 1:2. The isolated ozanimod salt can be separated by any suitable technique, for example by filtration or using a centrifuge.

The invention will be further described with reference to the following examples.

EXAMPLES

Nuclear magnetic resonance spectroscopy (NMR) was performed using Avance III 400 MHz NMR spectrometer.

XRPD spectrum was obtained using the following measurement conditions:

Panalytical Empyrean diffractometer with Θ/2Θ geometry (transmission mode), equipped with a PixCell 3D detector:

| | |
|---|---|
| Start angle (2θ): | 2.0° |
| End angle (2θ): | 35.0° |
| Step size: | 0.026° |
| Scan speed: | 0.0955°/seconds |
| Radiation type: | Cu |
| Radiation wavelengths: | 1.5406 Å (Kα1), primary monochromator used |
| Divergence slit: | 1/2° |
| Antiscatter slit: | 1/2° |
| Soller slit: | 0.02 rad |
| Detector slit: | 7.5 mm |
| Rotation speed: | 30 rpm |

Example 1:
(S)-1-amino-2,3-dihydro-1H-indene-4-carbonitrile hydrochloride

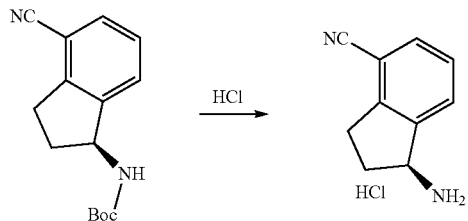 [SMILES: CC(C)(C)OC(=O)N[C@H]1CCc2c(C#N)cccc21 ; Cl ; N#Cc1cccc2c1CC[C@@H]2N ; Cl]

29.8 g of tert-Butyl (S)-(4-cyano-2,3-dihydro-1H-inden-1-yl)carbamate was suspended in 210 ml of MeOH followed by addition of 90 ml of 5 mol/l HCl solution in isopropanol. The reaction mixture was stirred at 45° C. for 3 h. The reaction mixture was concentrated to approximately 150 ml and transferred to 100 ml of methyl tert-butyl ether. The suspension was cooled to (0 to −5) ° C. and stirred for 20 minutes. The suspension was filtered, the filtration cake was washed with 2×50 ml of cold methyl tert-butyl ether. The obtained material was dried at room temperature (20-25° C.) to give 20.5 g of the title compound (yield 91%, HPLC purity 99.8%).

Example 2: (S)-1-(2-oxooxazolidin-3-yl)-2,3-dihydro-1H-indene-4-carbonitrile

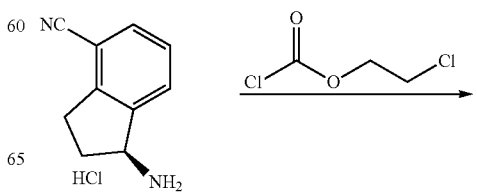

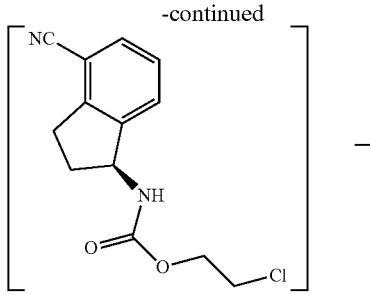

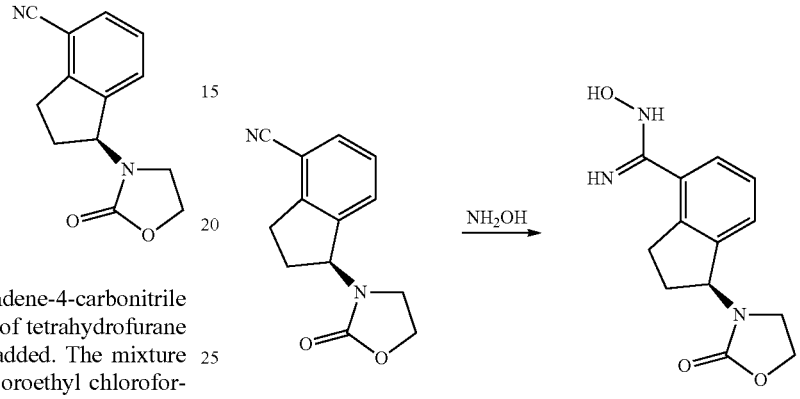

2 g of (S)-1-amino-2,3-dihydro-1H-indene-4-carbonitrile hydrochloride were suspended in 15 ml of tetrahydrofurane (THF). 3.15 ml of triethylamine were added. The mixture was cooled to 0-5° C. 1.27 ml of 2-Chloroethyl chloroformate was added drop-wise to the mixture. The mixture was stirred at a temperature between 0-5° C. for additional one hour to obtain a suspension. The suspension was filtered and the filtration cake was washed with 4 ml THF. Combined filtrates were cooled to 0-5° C. and 4 ml of 25% in methanol solution of sodium methanolate were added. The mixture was stirred at 0-5° C. for 1.5 hours. Then it was warmed to 20-25° C. and concentrated under vacuum. The residue was diluted with 10 ml of water and 15 ml of ethylacetate (EtOAc). The phases were separated and the water phase was extracted with additional 15 ml of EtOAc. Combined organic extracts were dried over MgSO$_4$ and evaporated to dryness to give 1.99 g of (S)-1-(2-oxooxazolidin-3-yl)-2,3-dihydro-1H-indene-4-carbonitrile (85% of the theoretical yield, purity HPLC IN 97.7%). The structure of (S)-1-(2-oxooxazolidin-3-yl)-2,3-dihydro-1H-indene-4-carbonitrile was confirmed by NMR.

Example 3: (S)—N-hydroxy-1-(2-oxooxazolidin-3-yl)-2,3-dihydro-1H-indene-4-carboximidamide 2 g of (S)-1-(2-oxooxazolidin-3-yl)-2,3-dihydro-1H-indene-4-carbonitrile were dissolved in 25 ml of ethanol (EtOH) followed by addition of 0.78 ml of 50% aqueous solution of hydroxylamine. The mixture was heated at 85° C. for 7 hours, then it was cooled to 20-25° C. and filtered. The filtration cake was washed with 5 ml of ethanol. The obtained material was dried at 20-25° C. to give 1.8 g of (S)—N-hydroxy-1-(2-oxooxazolidin-3-yl)-2,3-dihydro-1H-indene-4-carboximidamide (80% of the theoretical yield, purity HPLC IN 98.8%). The structure of (S)—N-hydroxy-1-(2-oxooxazolidin-3-yl)-2,3-dihydro-1H-indene-4-carboximidamide was confirmed by NMR.

Example 4: (S)—N-hydroxy-1-(2-oxooxazolidin-3-yl)-2,3-dihydro-1H-indene-4-carboximidamide 2 g of (S)-1-(2-oxooxazolidin-3-yl)-2,3-dihydro-1H-indene-4-carbonitrile was dissolved in 18 ml of EtOH and 2 ml of THF. The mixture was heated to 55° C. followed by addition of 0.78 ml of 50% aqueous solution of hydroxylamine. The mixture was heated at (70 to 75) ° C. for 7 hours, then it was cooled to (0 to −5) ° C. and stirred for 20 min. Then, the suspension was filtered, the filtration cake was washed with 2×1 ml of cold ethanol. The obtained material was dried at room temperature to give 2.1 g of title compound (yield 92%, HPLC purity 98.8%).

Example 5: (S)—N-hydroxy-1-(2-oxooxazolidin-3-yl)-2,3-dihydro-1H-indene-4-carboximidamide, One Pot Reaction

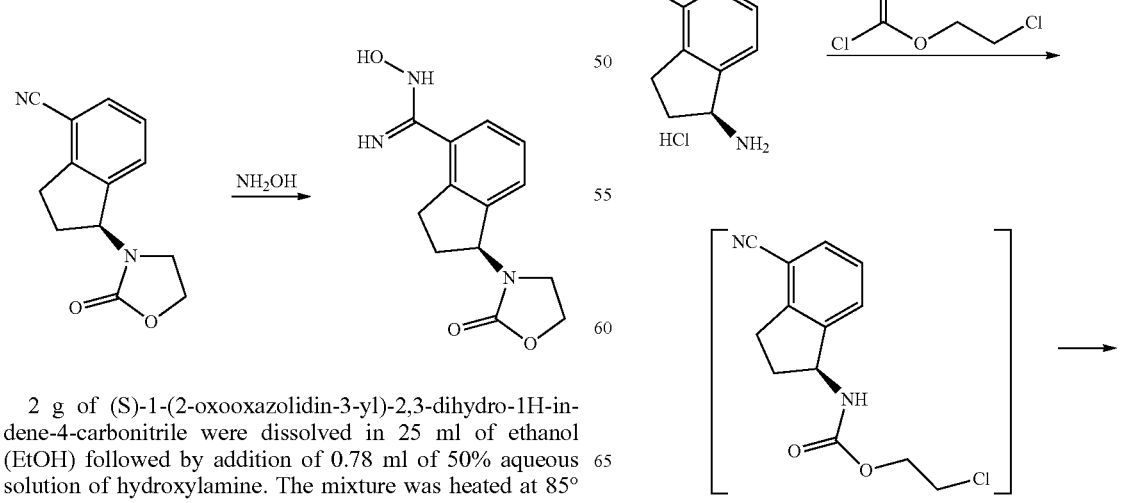

-continued

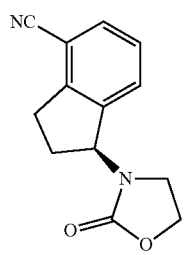 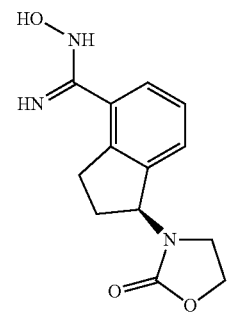

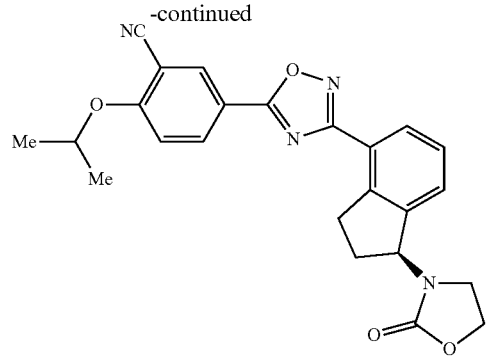

35 g of (S)-1-amino-2,3-dihydro-1H-indene-4-carbonitrile hydrochloride was mixed with 245 ml of 2-Methyltetrahydrofurane. Tot the mixture a solution of 52.4 g of potassium carbonate in 105 ml of water was added in one portion with stirring to obtain two phase mixture. The temperature of the mixture was set to 15° C. and 22.27 ml of 2-chloroethyl carbonochloridate was added. Temperature of the mixture was maintained below 35° C. during the addition. The temperature of the mixture was set to 22° C. and the mixture was stirred for additional 30 minutes. Then temperature of the mixture was set to 70° C. and the mixture was stirred to obtain a solution. The phases were separated at a temperature 60-70° C. Then 105 ml of 5M potassium hydroxide water solution was added in one portion, followed by addition of 1.75 g of tetrabutylammonium chloride. The two phase mixture was then vigorously stirred for 1 hour. The phases were separated while keeping the temperature of the mixture between 50-70° C. Organic phase was washed with 60 ml of water. 105 ml of isopropanol was added followed by 16.5 ml 50% water solution of hydroxylamine. The mixture was stirred for 24 hours at 65° C., then cooled to 0-5° C. and filtered. The filtration cake was washed with 2×50 ml of isopropanol and the product was dried at 45° C. in vacuum overnight to give (S)—N-hydroxy-1-(2-oxooxazolidin-3-yl)-2,3-dihydro-1H-indene-4-carboximidamide in yield 91% and 99.4% purity (HPLC IN).

Example 6: (S)-2-isopropoxy-5-(3-(1-(2-oxooxazolidin-3-yl)-2,3-dihydro-1H-inden-4-yl)-1,2,4-oxadiazol-5-yl)benzonitrile

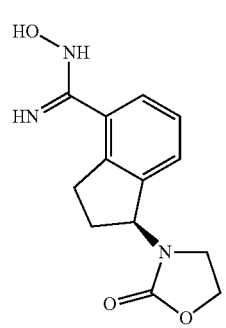 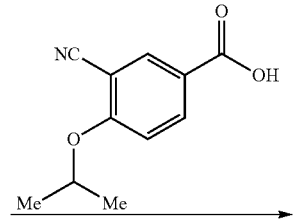

4.12 g of 3-Cyano-4-isopropoxybenzoic acid were dissolved in 25 ml of N-methylpyrrolidone (NMP) a temperature 20-25° C. To the mixture 3.72 g of 1,1'-carbonyldiimidazole were added. The reaction mixture was stirred at 20-25° C. for 2 hours. Afterwards, 5 g of (S)—N-hydroxy-1-(2-oxooxazolidin-3-yl)-2,3-dihydro-1H-indene-4-carboximidamide were added. The reaction mixture was stirred at 20-25° C. for 30 minutes. Then it was heated to 80° C. and stirred at this temperature for 18 hours. To the mixture 10 ml of water was added and the suspension was cooled to 0-5° C., stirred at this temperature for 30 minutes. The suspension was filtered and the filtration cake was washed with 3 ml of methanol. The obtained solid material was dried at 20-25° C. room temperature to give 4.8 g of (S)-2-isopropoxy-5-(3-(1-(2-oxooxazolidin-3-yl)-2,3-dihydro-1H-inden-4-yl)-1,2,4-oxadiazol-5-yl)benzonitrile (70% of theoretical yield, purity HPLC IN 99.5%). The structure of (S)-2-isopropoxy-5-(3-(1-(2-oxooxazolidin-3-yl)-2,3-dihydro-1H-inden-4-yl)-1,2,4-oxadiazol-5-yl)benzonitrile was confirmed by NMR.

Example 7: 5-[3-[1(S)-(2-Hydroxyethylamino)-2,3-dihydro-1H-inden-4-yl]-1,2,4-oxadiazol-5-yl]-2-isopropoxybenzonitrile (ozanimod)

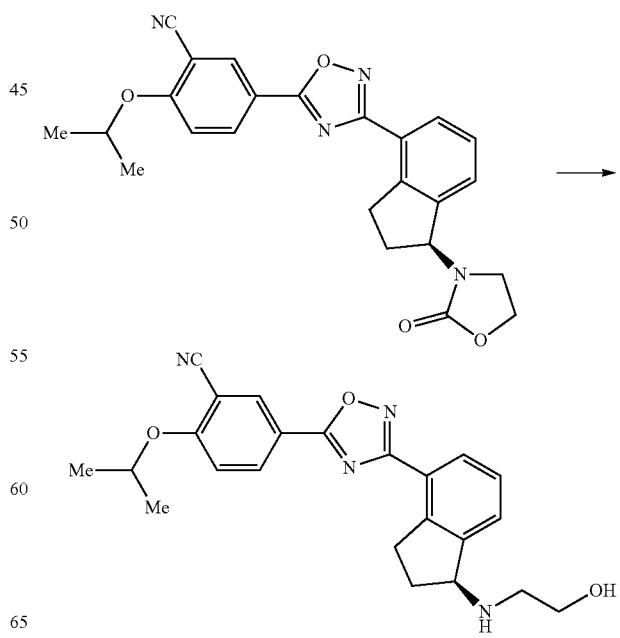

1 g of (S)-2-isopropoxy-5-(3-(1-(2-oxooxazolidin-3-yl)-2,3-dihydro-1H-inden-4-yl)-1,2,4-oxadiazol-5-yl)benzonitrile was dissolved in 6.5 ml of tetrahydrofurane, followed by addition of 1.5 ml of trimethylsilanol and 3.5 ml of solution of potassium trimethylsilanoate in THF (2 mol/l solution). The mixture was heated at 60° C. and stirred at this temperature for one hour. 10 ml of water was added. The mixture was stirred at 50-60° C. until complete dissolution followed by addition of 10 ml of isopropylacetate. The mixture was stirred at the same temperature for additional 10 min and filtered over celite pad. The filtrate was heated to 60° C. The phases were separated. Water phase was extracted with 8 ml of isopropylacetate. Combined organic phases were then evaporated to dryness to give title compound (0.85 g, 90% of the theoretical yield, HPLC IN purity 92%).

Example 8: 5-[3-[1(S)-(2-Hydroxyethylamino)-2,3-dihydro-1H-inden-4-yl]-1,2,4-oxadiazol-5-yl]-2-isopropoxybenzonitrile (ozanimod)

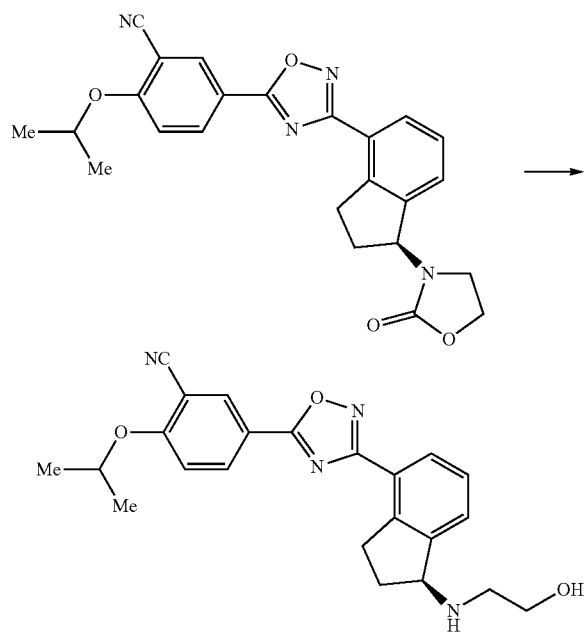

19.5 g of potassium tert-butoxide were dissolved in 250 ml of tetrahydrofurane. The solution was cooled to 15° C. and 84 ml of trimethylsilanol was added slowly. Temperature during addition was maintained below 30° C. The resulting mixture was stirred for 5 min at 20-25° C. 25 g of (S)-2-isopropoxy-5-(3-(1-(2-oxooxazolidin-3-yl)-2,3-dihydro-1H-inden-4-yl)-1,2,4-oxadiazol-5-yl)benzonitrile was added. The reaction mixture was heated to 60° C. and stirred for 1.5 h. 250 ml of water was added. The mixture was stirred at 50-60° C. until complete dissolution followed by addition of 250 ml of isopropylacetate. The mixture was stirred at the same temperature for additional 10 min and filtered over celite pad. The filtrate was heated to 60° C. The phases were separated. Water phase was extracted with 200 ml of isopropylacetate. Combined organic phases were then evaporated to dryness to give title compound in yield 91% and 92% purity.

Example 9: Salts of Ozanimod Prepared from Isopropanol

Ozanimod salts selected from salts with sulfuric acid or citric acid or formic acid or benzoic acid or acetic acid or oxalic or $H_3PO_4$ or hydrochloric acid were prepared by following procedure: 20 mg of ozaninod were suspended in 0.6 ml of isopropanol and the mixture was heated to 85° C. Corresponding acid was added to the mixture. The molar ratio between ozanomid and the acid was 1:1.05. The mixture was heated to 90° C. and stirred at this temperature for 15 minutes. The mixture was cooled to 20° C. and stirred at this temperature for 60 minutes. The mixture was filtrated and the filtrated mass was washed with 0.1 ml of cold isopropanol and dried to provide the relevant ozanimod salt. The yield of preparation (% of theoretical yield, based on starting ozanimod) and XRPD data are summarized in following table.

Figure 2:
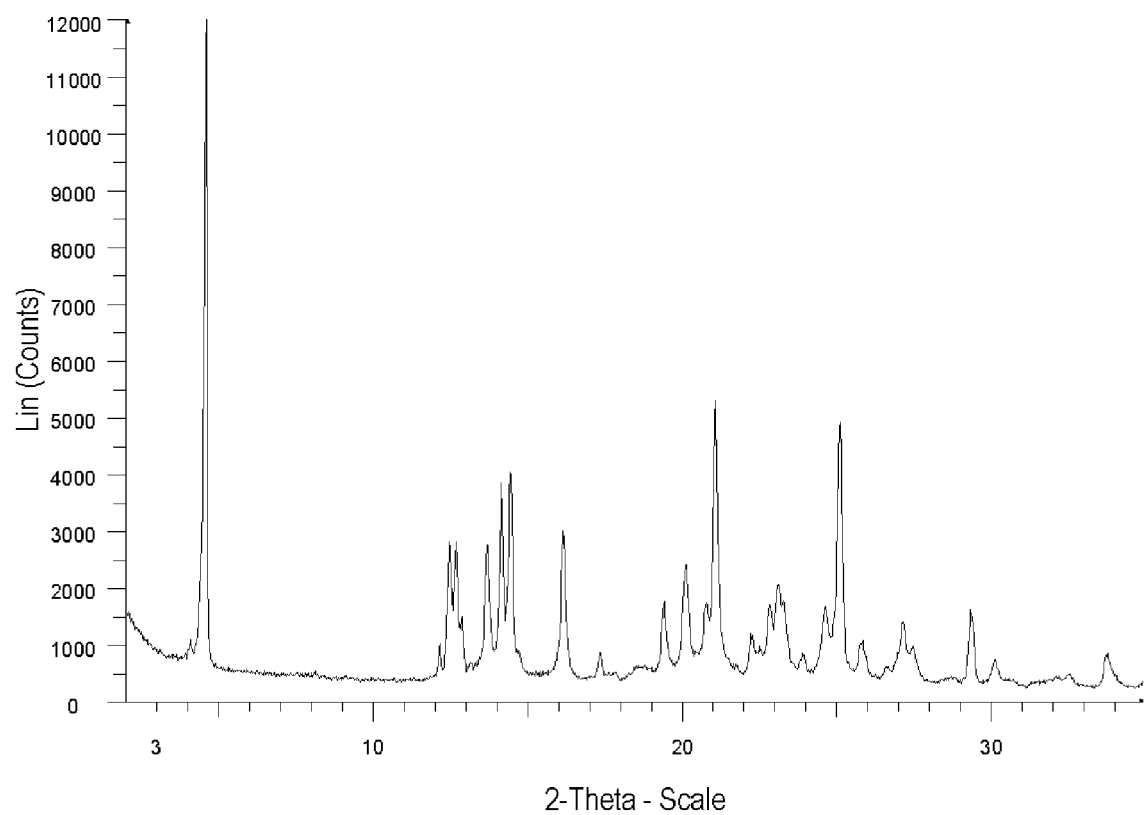
FIG. 2 depicts the X-Ray Powder Diffractogram (XRPD) of ozanimod salt with citric acid obtainable according to the Example 7.
Figure 3:
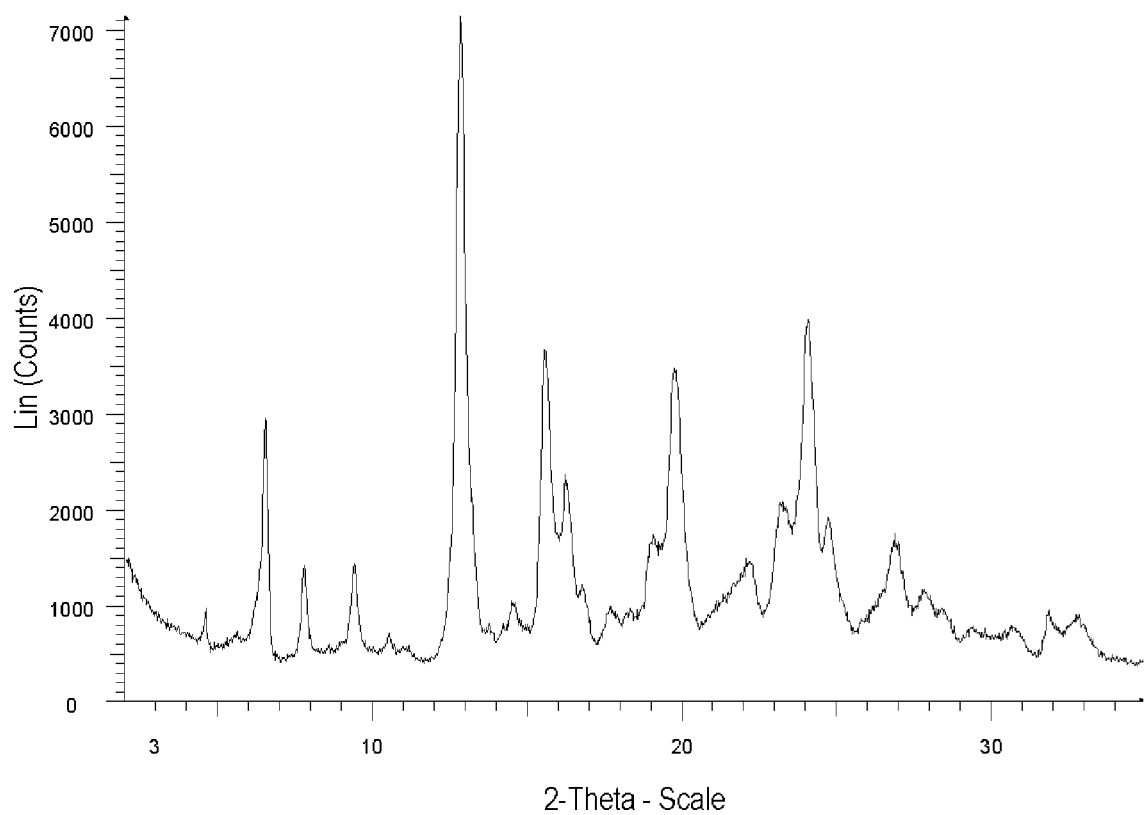
FIG. 3 depicts the X-Ray Powder Diffractogram (XRPD) of ozanimod salt with formic acid obtainable according to the Example 7.
Figure 4:
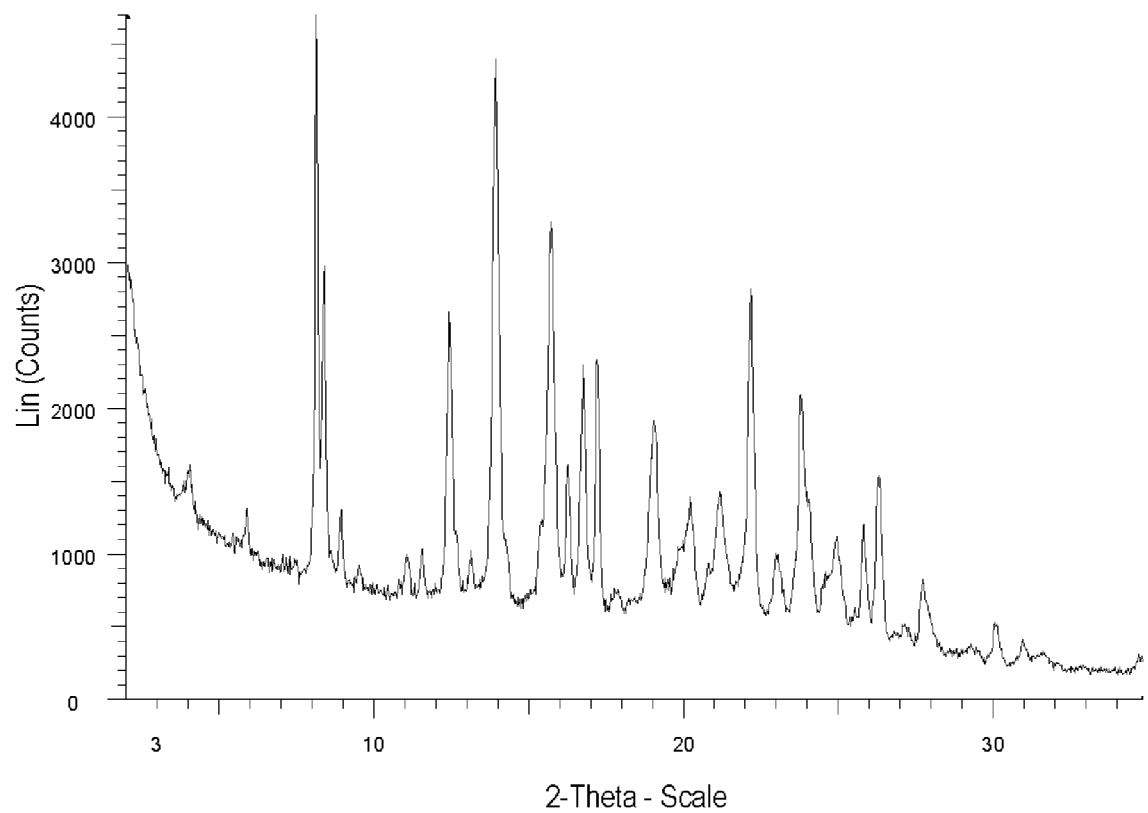
FIG. 4 depicts the X-Ray Powder Diffractogram (XRPD) of ozanimod salt with benzoic acid obtainable according to the Example 7.
Figure 5:
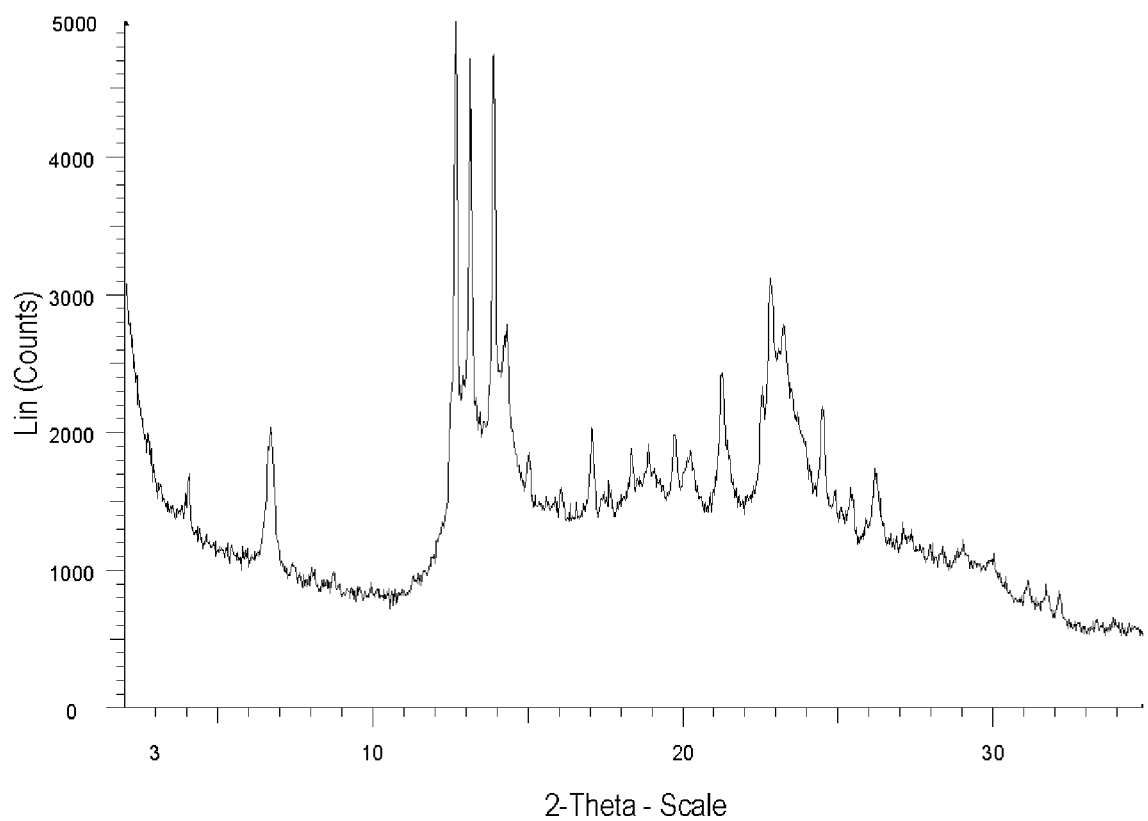
FIG. 5 depicts the X-Ray Powder Diffractogram (XRPD) of ozanimod salt with acetic acid obtainable according to the Example 7.
Figure 6:
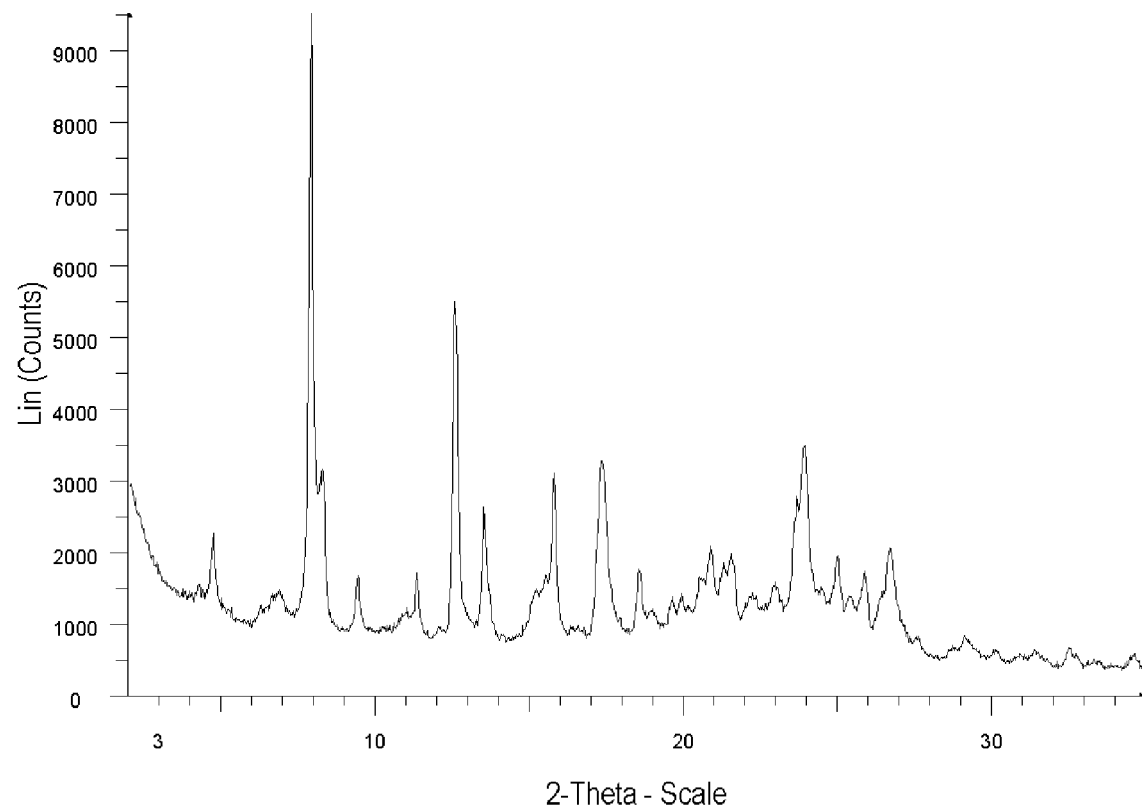
FIG. 6 depicts the X-Ray Powder Diffractogram (XRPD) of ozanimod salt with oxalic acid obtainable according to the Example 7.
Figure 7:
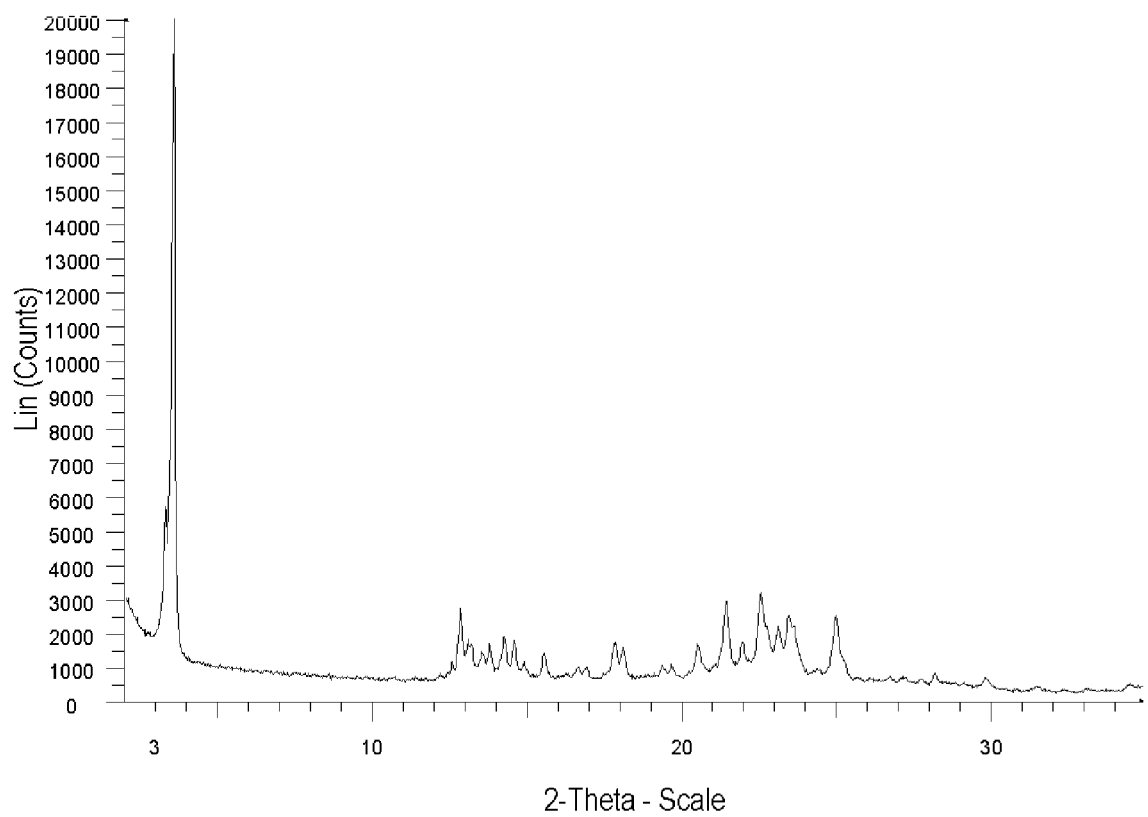
FIG. 7 depicts the X-Ray Powder Diffractogram (XRPD) of ozanimod salt with $H_3PO_4$ obtainable according to the Example 7.
Figure 8:
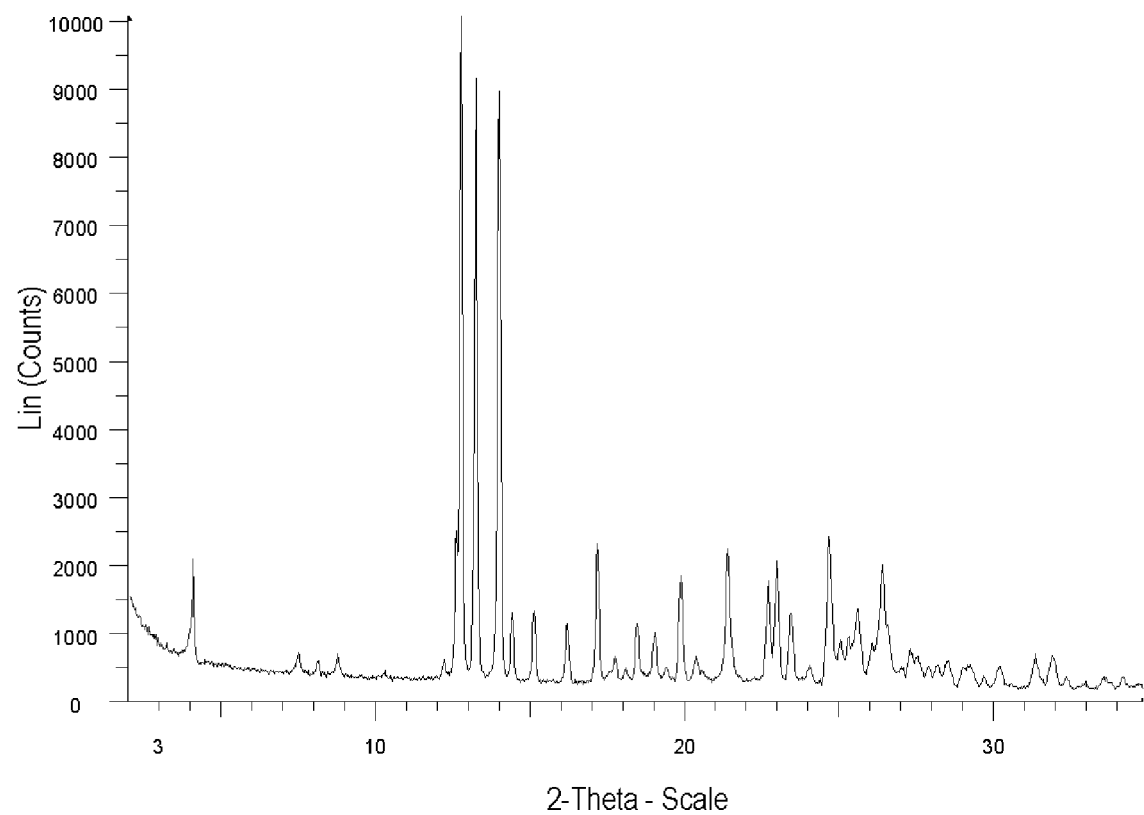
FIG. 8 depicts the X-Ray Powder Diffractogram (XRPD) of ozanimod salt with HCl obtainable according to the Example 7.

| Used acid | Yield of preparation | Corresponding XRPD pattern |
|---|---|---|
| $H_2SO_4$ | 80% | FIG. 1 |
| citric acid | 92% | FIG. 2 |
| formic acid | 94% | FIG. 3 |
| benzoic acid | 77% | FIG. 4 |
| acetic acid | 52% | FIG. 5 |
| oxalic acid | 98% | FIG. 6 |
| $H_3PO_4$ | 100% | FIG. 7 |
| HCl | 97% | FIG. 8 |

Example 10: Salts of Ozanimod Prepared from 2-Methyl Tetrahydrofurane

Ozanimod salts selected from salts with sulfuric acid or citric acid or formic or hydrochloric acid were prepared by following procedure:

30 mg of ozaninod were suspended in 4.5 ml of 2-methyl tetrahydrofurane and the mixture was heated to 85° C. Corresponding acid was added. The molar ratio between ozanomid and the acid was 1:1.05. The mixture was heated to 90° C. and stirred at this temperature for 30 minutes. The mixture was cooled to 20° C. and stirred at this temperature for 60 minutes. The mixture was filtrated and the filtered mass was washed with 0.5 ml of cold 2-methyl tetrathydrofurane and dried to provide the relevant ozanimod salt. The yields of preparation (% of theoretical yield, based on starting ozanimod) and XRPD data are summarized in following table.

Figure 9:
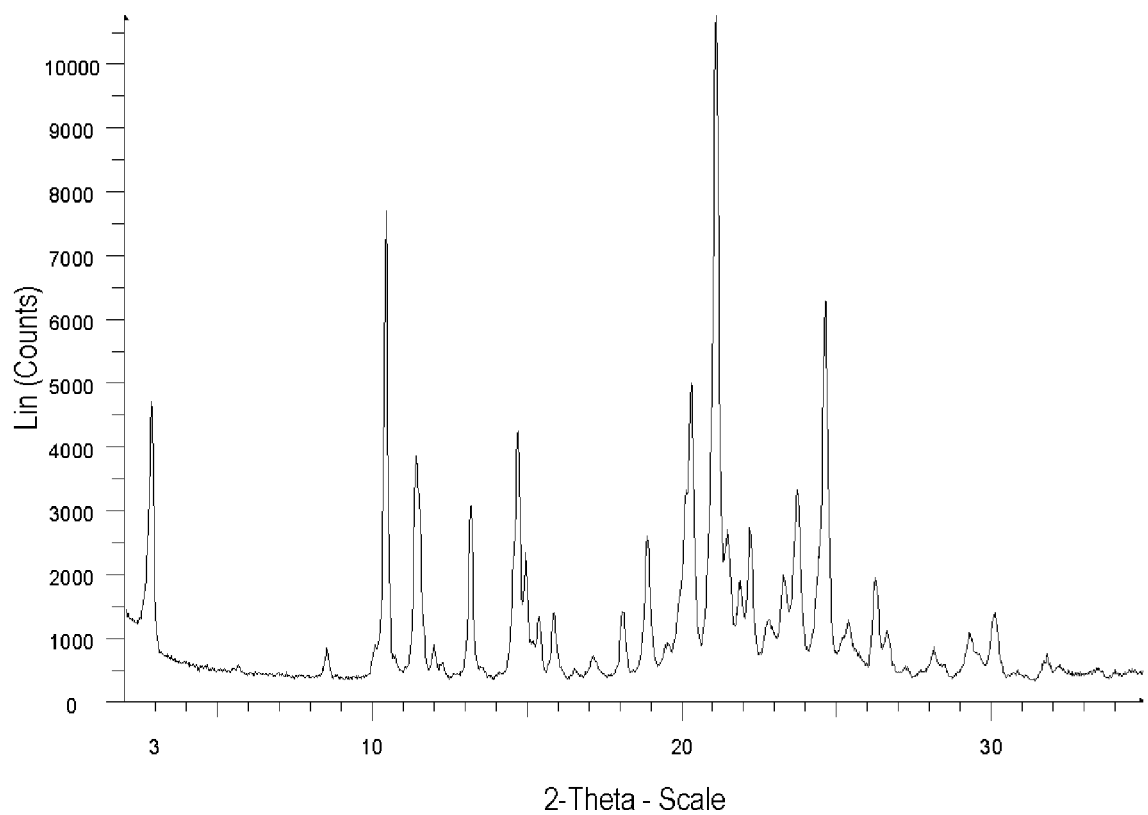
FIG. 9 depicts the X-Ray Powder Diffractogram (XRPD) of ozanimod salt with $H_2SO_4$ obtainable according to the Example 8.
Figure 10:
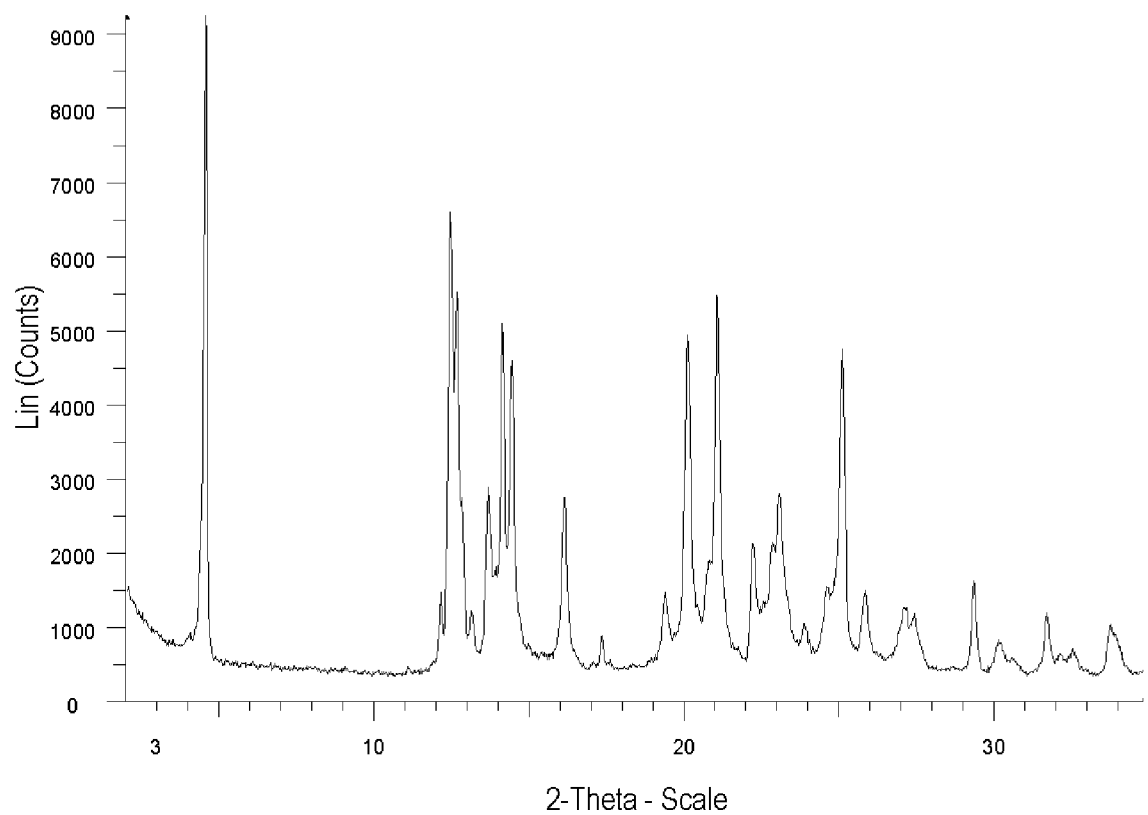
FIG. 10 depicts the X-Ray Powder Diffractogram (XRPD) of ozanimod salt with citric acid obtainable according to the Example 8.
Figure 11:
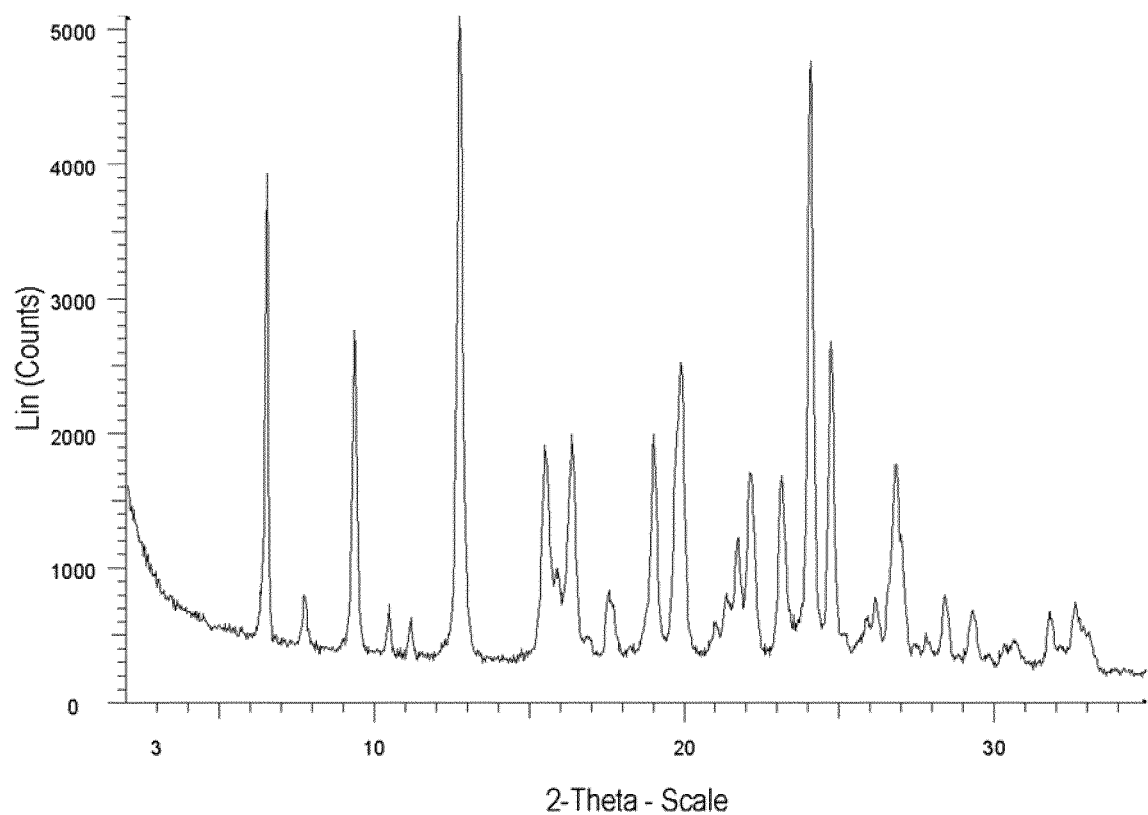
FIG. 11 depicts the X-Ray Powder Diffractogram (XRPD) of ozanimod salt with formic acid obtainable according to the Example 8.
Figure 12:
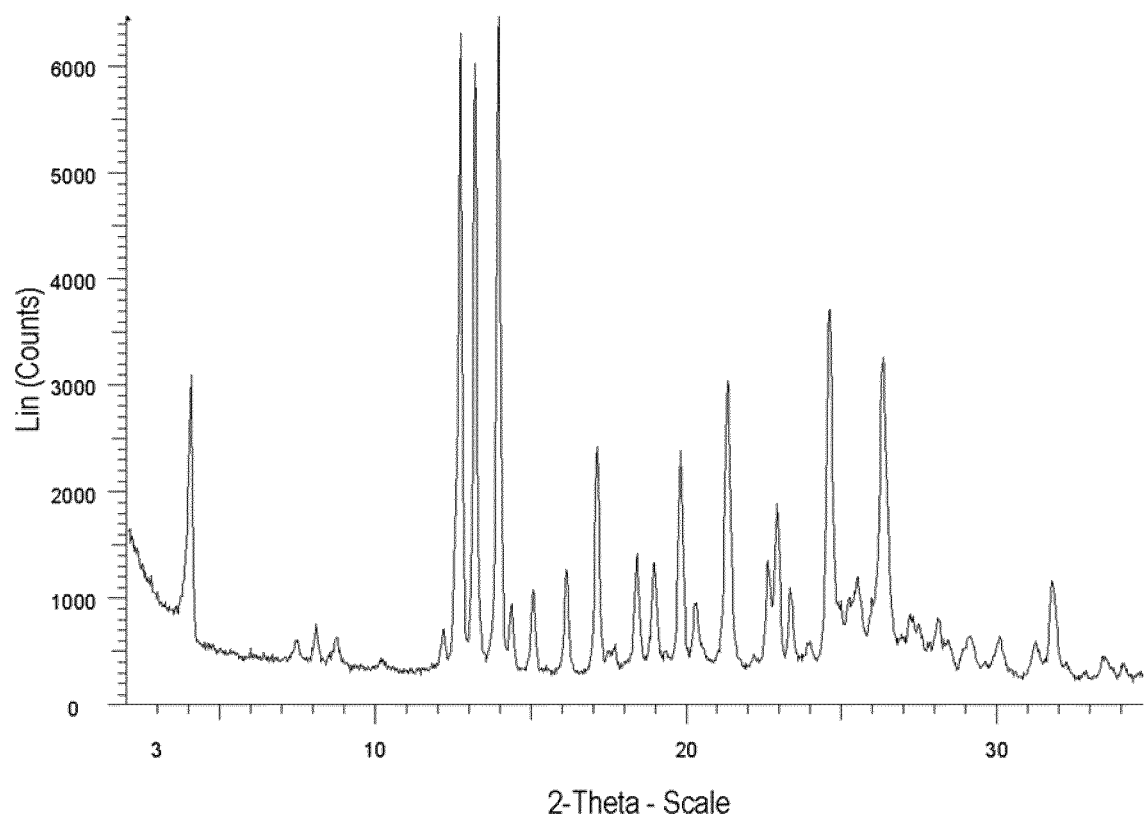
FIG. 12 depicts the X-Ray Powder Diffractogram (XRPD) of ozanimod salt with HCl obtainable according to the Example 8.

| Used acid | Yield of preparation | Corresponding XRPD pattern |
|---|---|---|
| $H_2SO_4$ | 96% | FIG. 9 |
| citric acid | 75% | FIG. 10 |
| formic acid | 72% | FIG. 11 |
| HCl | 95% | FIG. 12 |

Figure 13:
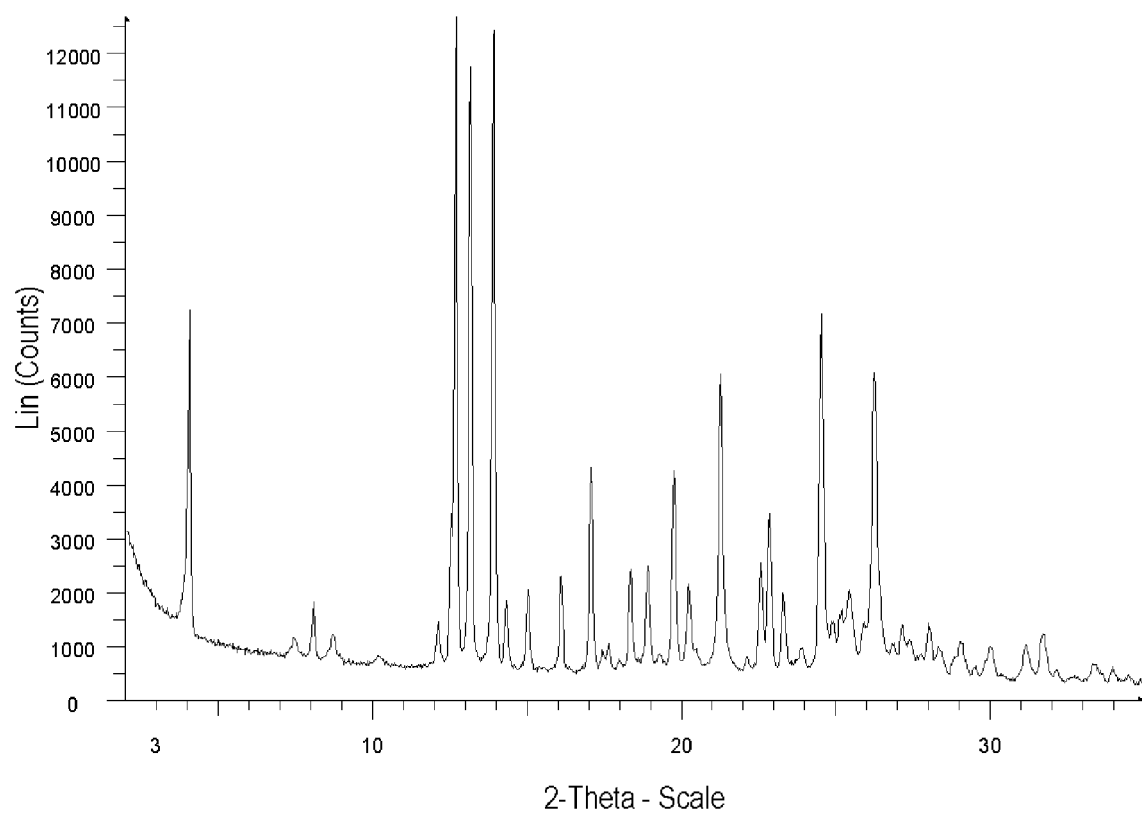
FIG. 13 depicts the X-Ray Powder Diffractogram (XRPD) of ozanimod salt with HCl obtainable according to the Example 8.

Example 11: Ozanimod HCl Salt 50 mg of ozanimod were suspended in 2 ml of methanol and 0.035 ml of 15.7% solution of HCl in dioxane were added. The mixture was heated to 90° C. and stirred at this temperature for 15 minutes. The mixture was cooled to 20° C. and stirred at this temperature for 60 minutes. The mixture was filtrated and the mass was washed with 0.1 ml of cold methanol and dried to obtain 41 mg of ozanimod HCl salt. XRPD pattern of obtained solid salt is depicted in FIG. 13.

Example 12: Salts of Ozanimod Prepared from Water

Ozanimod salts selected from salts with sulfuric acid or benzoic acid or HCl were prepared by following procedure:

20 mg of ozanimod were suspended in 0.5 ml of water and the mixture was heated to 85° C. Corresponding acid was added. The molar ratio between ozanimod and the acid was 1:1.05. The mixture was heated to 90° C. and stirred at this temperature for 30 minutes. The mixture was cooled to 20° C. and stirred at this temperature for 60 minutes. The mixture was filtrated and the filtrated mass was washed with 0.2 ml of cold water and dried to provide the relevant ozanimod salt. The yields of preparation (% of theoretical yield, based on starting ozanimod) and XRPD data are summarized in following table.

Figure 14:
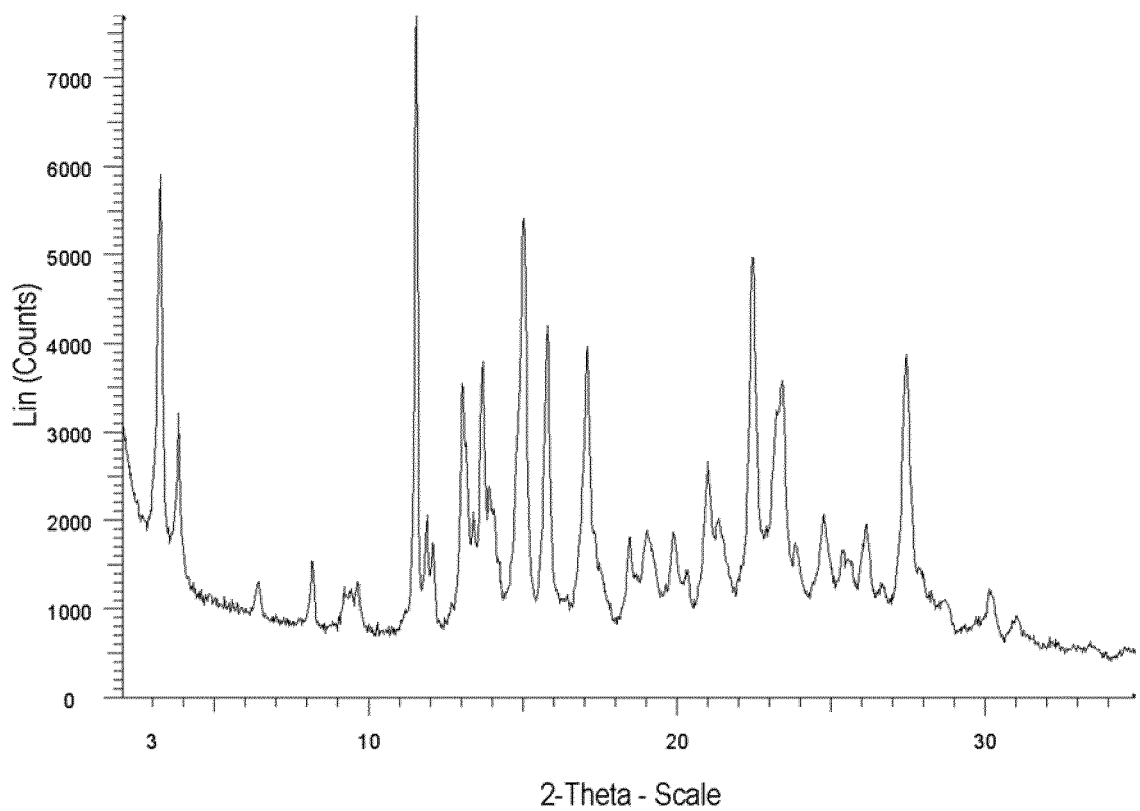
FIG. 14 depicts the X-Ray Powder Diffractogram (XRPD) of ozanimod salt with $H_2SO_4$ obtainable according to the Example 10.
Figure 15:
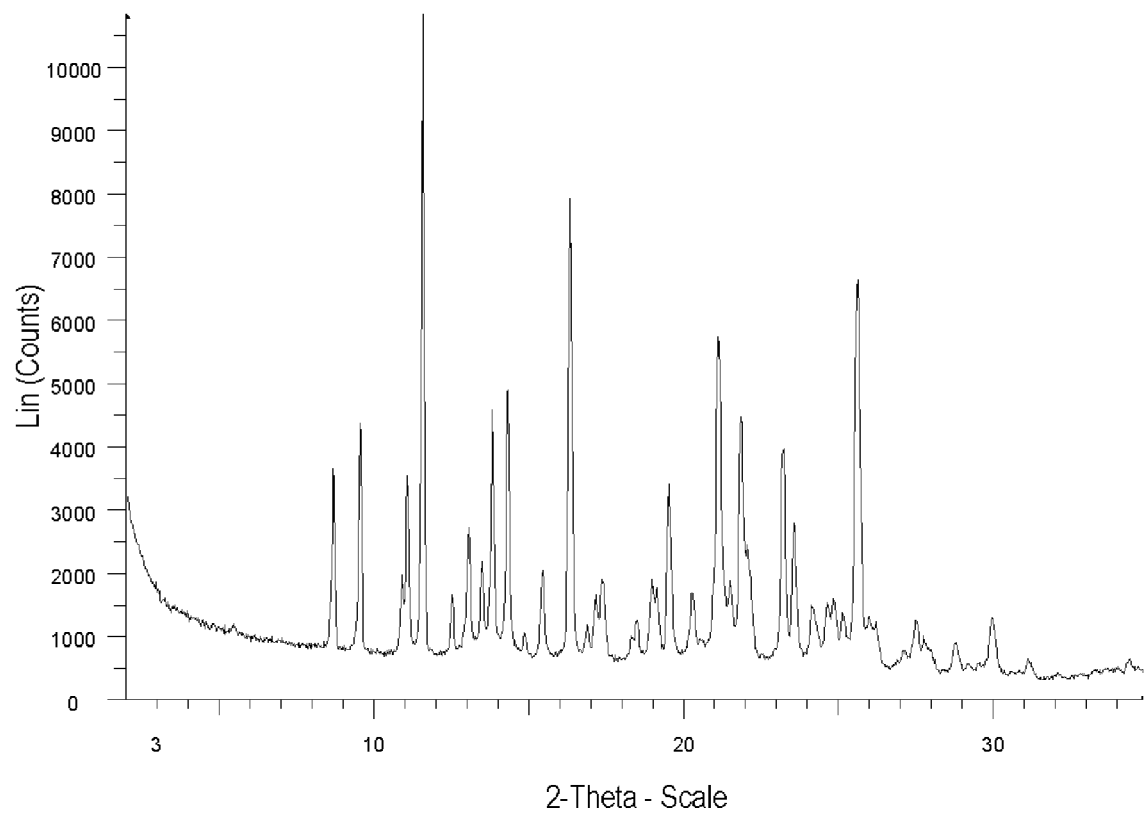
FIG. 15 depicts the X-Ray Powder Diffractogram (XRPD) of ozanimod salt with benzoic acid obtainable according to the Example 10.
Figure 16:
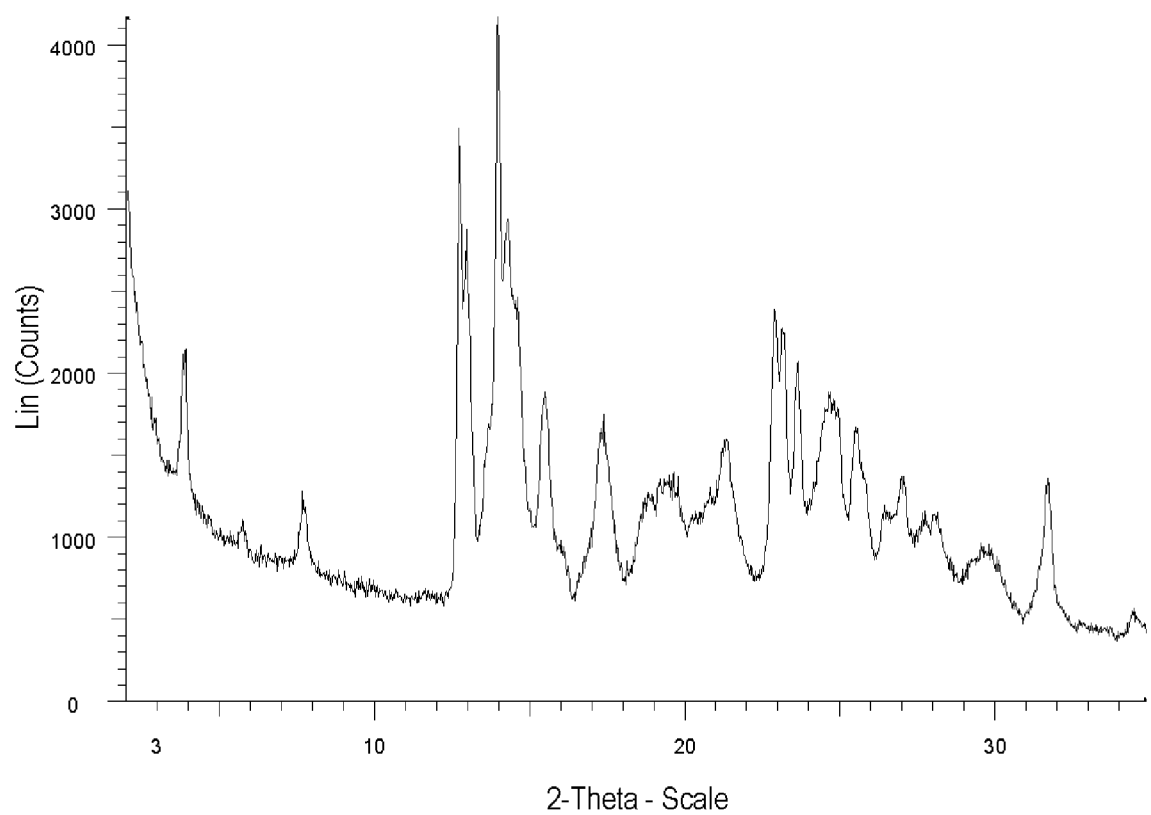
FIG. 16 depicts the X-Ray Powder Diffractogram (XRPD) of ozanimod salt with HCl obtainable according to the Example 10.

| Used acid | Yield of preparation | Corresponding XRPD pattern |
|---|---|---|
| $H_2SO_4$ | 64% | FIG. 14 |
| benzoic acid | 73% | FIG. 15 |
| HCl | 55% | FIG. 16 |

The invention claimed is:

1. A process for preparation of compound of formula (1) or a salt thereof,

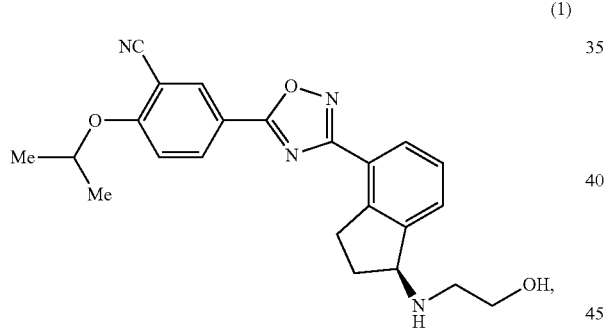

(1)

comprising:
I) Reacting a compound (2) or a salt thereof with compound (3),

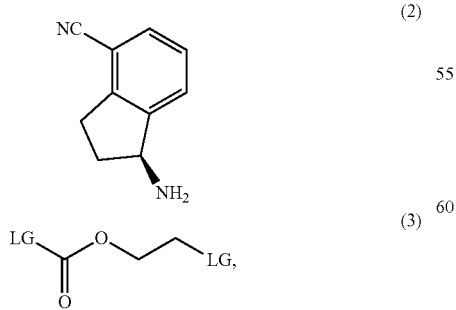

(2)

(3)

wherein LG is a leaving group independently selected from Cl or Br or I or an ester selected from methoxy or ethoxy or tosylate or mesylate or benzenesulfonate or triflate in a solvent in a presence of a base;

II) Adding a base selected from an alcoholate or a hydride or an organometal or a hydroxide or a salt of an organic amide or 1,8-Diazabicyclo[5.4.0]undec-7-ene or 1,5-Diazabicyclo(4.3.0)non-5-ene or 1,4-diazabicyclo[2.2.2]octane into the reaction mixture of step I) to provide compound (4),

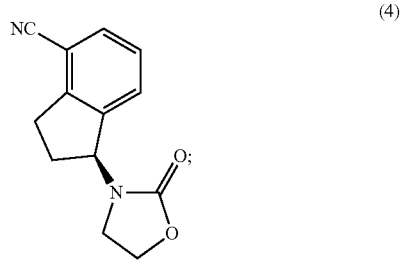 [SMILES: N#Cc1cccc2c1CC[C@@H]2N1CCOC1=O]

(4)

III) Reacting compound (4) with hydroxylamine or a salt thereof in a solvent to provide compound (5),

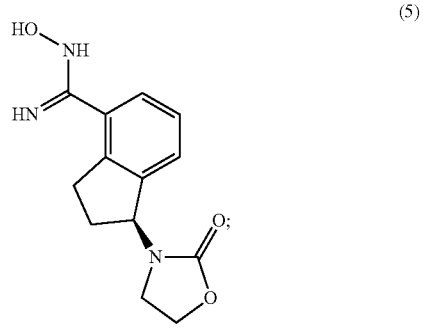 [SMILES: N=C(NO)c1cccc2c1CC[C@@H]2N1CCOC1=O]

(5)

IV) Reacting compound (5) with compound (6) in a presence of coupling agent in a solvent to provide compound (7),

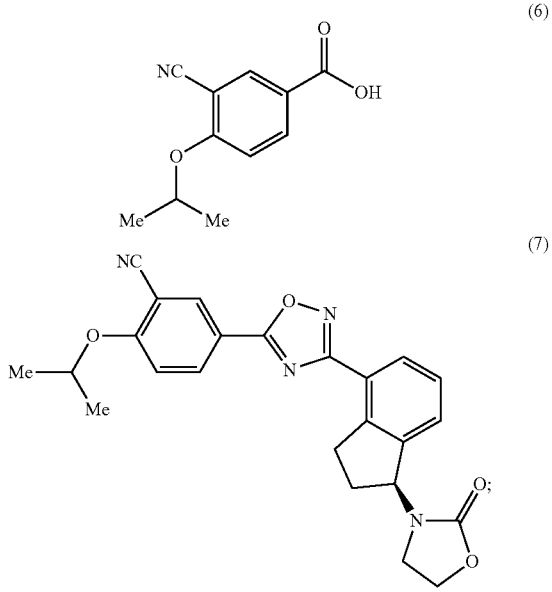

(6)

(7)

V) Reacting compound (7) in a presence of a compound of formula (R)₃SiOM, wherein R is selected from R₁-R₅ alkyl or aryl and M is selected from Na or K or Li in a solvent to provide compound (1).

2. The process according to claim 1 wherein the compound (3) is:

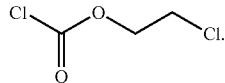

3. The process according to claim 1 wherein the step I) is performed in a solvent selected from tetrahydrofurane or 2-methyl tetrahydrofurane or toluene or acetonitrile or dimethylformamide.

4. The process according to claim 3 wherein the solvent is used in a mixture with water.

5. The process according to claim 1 wherein the base used in step I) is an amine or 1,8-Diazabicyclo[5.4.0]undec-7-ene or 1,5-Diazabicyclo(4.3.0)non-5-ene or 1,4-diazabicyclo[2.2.2]octane or a phosphazene base or an organometal or an amide or a hydroxide or a carbonate or a hydrogencarbonate an alcoholate or a hydride or an organometal or a salt of an organic amide.

6. The process according to claim 5 wherein the base is triethylamine or potassium carbonate.

7. The process according to claim 1 wherein the base is step II) is selected from sodium or potassium methanolate or sodium or potassium ethanolate or sodium or potassium hydride or butyl lithium, or sodium or potassium hydroxide or sodium bis(trimethylsilyl)amide or lithium bis(trimethylsilyl)amide or sodium amide or lithium diisopropyl amide or lithium diethylamide.

8. The process according to claim 1 wherein the solvent in step II) is an alcohol or tetrahydrofurane or 2-methyl tetrahydrofurane.

9. The process according to claim 8 wherein the solvent is used in a mixture with water.

10. The process according to claim 1 wherein the salt of hydroxylamine in step III) is HCl salt.

11. The process according to claim 1 wherein the solvent in step III) is an alcohol or acetonitrile or 2-methyl tetrahydrofurane or a mixture thereof.

12. The process according to claim 1 wherein the coupling agent used in step IV) is selected from 1,1'-Carbonyldiimidazole, dicyclohexylcarbodiimide, diisopropylcarbodiimide, 1-hydroxy-benzotriazole, 1-hydroxy-7-aza-benzotriazole, benzotriazol-1-yloxy)tris(dimethylamio)phosphonium hexafluorophosphate, benzotriazol-1-yloxy)tris(pyrrolidino) phosphonium hexafluorophosphate, (bromo)tris(pyrrolidino)phosphonium hexafluorophosphate, (bromo)tris(dimethylamio) phosphonium hexafluorophosphate, 2-(1H-benzotriazole-1-yl)-1, 1,3,3-tetramethyluronium hexafluorophosphate , N-(3-Dimethylaminopropyl)-N'-ethylcarbodiimide hydrochloride or a cyclic alkyltriphosphonate anhydride of general formula,

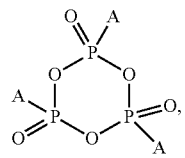

wherein A is C₁-C₃ alkyl group and a combination thereof.

13. The process according to claim 12 wherein the coupling agent is 1,1'-Carbonyldiimidazole.

14. The process according to claim 1 wherein the suitable solvent in step IV) is N-methyl-pyrrolidone or dimethylformamide or dimethylacetamide or dimethyl sulfoxide or tetrahydrofurane or 2-methyl tetrahydrofurane and a mixture thereof.

15. The process according to claim 1 wherein the compound of formula (R)₃SiOM used in step V) is selected from (R)₃SiONa or (R)₃SiOK.

16. The process according to claim 15 wherein the compound of formula (R)₃SiOM is sodium or potassium trimethylsilinoate.

17. The process according to claim 1 wherein the solvent used in step V) is selected from tetrahydrofurane or 2-methyl tetrahydrofurane or dioxane or dimethoxyethane or anisol.

18. The process according to claim 1 wherein the step V) is performed in a presence of a compound of formula (R)₃SiOH, R is selected from R₁-R₅ alkyl or aryl.

19. The process according to claim 18 wherein the compound of formula (R)₃SiOH is selected from (R₁-R₅ alkyl) ₃SiOH.

20. The process according to claim 19 wherein the compound of formula (R)₃SiOH is (CH₃)₃SiOH.

21. The process according to claim 1 which further comprises isolating the compound of formula (4) in a solid form before performing step III).

22. The process according to claim 1 which further comprises isolating the compound of formula (5) in a solid form before performing step IV).

23. The process according to claim 1 which further comprises isolating the compound of formula (7) in a solid form before performing step V).

24. The process according to claim 1 wherein the salt of compound of formula (1) is selected from salt with sulfuric acid or citric acid or formic acid or benzoic acid or acetic acid or oxalic acid or phosphoric acid or HCl.

25. A compound of formula (4):

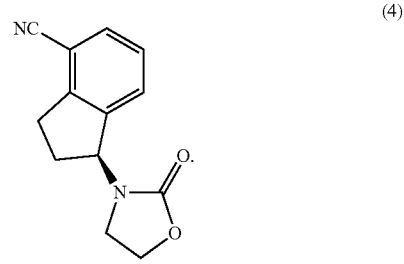 [SMILES: N#Cc1cccc2c1CC[C@@H]2N1CCOC1=O]

26. A compound of formula (5):
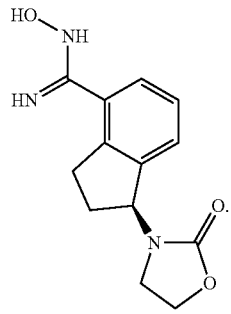
(5)